United States Patent
Pinsonneault

(10) Patent No.: US 10,635,783 B2
(45) Date of Patent: Apr. 28, 2020

(54) SYSTEMS AND METHODS FOR DETERMINING PATIENT ADHERENCE TO A PRESCRIBED MEDICATION PROTOCOL

(71) Applicant: McKesson Corporation, Irving, TX (US)

(72) Inventor: Roger G. Pinsonneault, Alpharetta, GA (US)

(73) Assignee: MCKESSON CORPORATION, Irving, TX (US)

( * ) Notice: Subject to any disclaimer, the term of this patent is extended or adjusted under 35 U.S.C. 154(b) by 813 days.

(21) Appl. No.: 14/312,471

(22) Filed: Jun. 23, 2014

(65) Prior Publication Data

US 2015/0371000 A1 Dec. 24, 2015

(51) Int. Cl.
G06F 19/00 (2018.01)
G16H 10/60 (2018.01)
G16H 20/10 (2018.01)

(52) U.S. Cl.
CPC ........ *G06F 19/3456* (2013.01); *G06F 19/328* (2013.01); *G16H 10/60* (2018.01); *G16H 20/10* (2018.01)

(58) Field of Classification Search
CPC ............... G06F 19/3456; G06F 19/322; G06F 19/3475; G06F 19/326; G06Q 50/22;
(Continued)

(56) References Cited

U.S. PATENT DOCUMENTS 4,674,041 A 6/1987 Lemon et al.
4,723,212 A 2/1988 Mindrum et al.
(Continued)

FOREIGN PATENT DOCUMENTS

CA 2482370 3/2006
WO 1995003569 2/1995
(Continued)

OTHER PUBLICATIONS

Hess, Lisa M., et al. "Measurement of adherence in pharmacy administrative databases: a proposal for standard definitions and preferred measures." Annals of pharmacotherapy 40.7-8 (2006): 1280-1288.*

(Continued)

*Primary Examiner* — Jonathan Durant
(74) *Attorney, Agent, or Firm* — Alston & Bird LLP

(57) ABSTRACT

Systems and methods are provided for determining patient adherence to a medication protocol by evaluating healthcare transactions. An e-prescription transaction can be received from a prescriber and evaluated to determine if the patient is to receive adherence analysis. If so, the e-prescription data can be stored and the e-prescription can be forwarded to a pharmacy. A healthcare claim transaction for a medication can be received from the pharmacy and forwarded on for adjudication. If approved, the claim transaction data can be evaluated to determine if it matches any stored e-prescription data records. Upon identifying a match, a prescription fill status notification can be generated and transmitted to the prescriber computer associated with the prescriber of the medication in the e-prescription. If the healthcare claim transaction is for a refill or a maintenance medication, a patient adherence level can be calculated and included in the prescription fill status notification.

14 Claims, 6 Drawing Sheets

(58) Field of Classification Search
CPC ........ G06Q 50/24; G16H 10/60; G16H 20/10;
G16H 20/00; G16H 50/30; G16H 50/70;
G16H 15/00
See application file for complete search history.

(56) References Cited

U.S. PATENT DOCUMENTS

| | | | |
|---|---|---|---|
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,237,620 A | 8/1993 | Deaton et al. | |
| 5,305,196 A | 4/1994 | Deaton et al. | |
| 5,327,508 A | 7/1994 | Deaton et al. | |
| 5,388,165 A | 2/1995 | Deaton et al. | |
| 5,430,644 A | 7/1995 | Deaton et al. | |
| 5,448,471 A | 9/1995 | Deaton et al. | |
| 5,588,649 A | 12/1996 | Blumberg et al. | |
| 5,592,560 A | 1/1997 | Deaton et al. | |
| 5,612,868 A | 3/1997 | Off et al. | |
| 5,621,812 A | 4/1997 | Deaton et al. | |
| 5,628,530 A | 5/1997 | Thornton | |
| 5,638,457 A | 6/1997 | Deaton et al. | |
| 5,642,485 A | 6/1997 | Deaton et al. | |
| 5,644,723 A | 7/1997 | Deaton et al. | |
| 5,649,114 A | 7/1997 | Deaton et al. | |
| 5,659,469 A | 8/1997 | Deaton et al. | |
| 5,675,662 A | 10/1997 | Deaton et al. | |
| 5,687,322 A | 11/1997 | Deaton et al. | |
| 5,832,457 A | 11/1998 | O'Brien | |
| 5,845,255 A | 12/1998 | Mayaud | |
| 5,857,175 A | 1/1999 | Day et al. | |
| 5,892,827 A | 4/1999 | Beach et al. | |
| 5,915,007 A | 6/1999 | Klapka | |
| 5,926,795 A | 7/1999 | Williams | |
| 5,970,469 A | 10/1999 | Scroggie et al. | |
| 5,974,399 A | 10/1999 | Giuliani et al. | |
| 6,014,634 A | 1/2000 | Scroggie et al. | |
| 6,021,392 A | 2/2000 | Lester et al. | |
| 6,026,370 A | 2/2000 | Jermyn | |
| 6,041,309 A | 3/2000 | Laor | |
| 6,055,573 A | 4/2000 | Gardenswartz et al. | |
| 6,067,069 A | 5/2000 | Krause | |
| 6,067,524 A | 5/2000 | Byerly et al. | |
| 6,012,035 A | 10/2000 | Freeman, Jr. et al. | |
| 6,185,541 B1 | 2/2001 | Scroggie et al. | |
| 6,195,612 B1 | 2/2001 | Pack-Harris | |
| 6,202,923 B1 | 3/2001 | Boyer et al. | |
| 6,205,455 B1 | 3/2001 | Umen | |
| 6,240,394 B1 | 5/2001 | Uecker | |
| 6,260,758 B1 | 7/2001 | Blumberg | |
| 6,278,979 B1 | 8/2001 | Williams | |
| 6,282,516 B1 | 8/2001 | Giuliani | |
| 6,298,330 B1 | 10/2001 | Gardenswartz et al. | |
| 6,304,849 B1 | 10/2001 | Uecker et al. | |
| 6,307,958 B1 | 10/2001 | Deaton et al. | |
| 6,321,210 B1 | 11/2001 | O'Brien et al. | |
| 6,334,108 B1 | 12/2001 | Deaton et al. | |
| 6,377,935 B1 | 4/2002 | Deaton et al. | |
| 6,424,949 B1 | 7/2002 | Deaton et al. | |
| 6,484,146 B2 | 11/2002 | Day et al. | |
| 6,578,003 B1 | 6/2003 | Camarda et al. | |
| 6,584,448 B1 | 6/2003 | Laor | |
| 6,684,195 B1 | 1/2004 | Deaton et al. | |
| 6,757,898 B1 | 6/2004 | Ilsen et al. | |
| 6,769,228 B1 | 8/2004 | Mahar | |
| 6,795,809 B2 | 9/2004 | O'Brien et al. | |
| 6,885,994 B1 | 4/2005 | Scroggie et al. | |
| 7,024,374 B1 | 4/2006 | Day et al. | |
| 7,058,584 B2 | 6/2006 | Kosinski et al. | |
| 7,058,591 B2 | 6/2006 | Giuliani et al. | |
| 7,155,397 B2 | 12/2006 | Alexander et al. | |
| 7,225,052 B2 | 5/2007 | Foote et al. | |
| 7,228,285 B2 | 6/2007 | Hull et al. | |
| 7,233,913 B2 | 6/2007 | Scroggie et al. | |
| 7,309,001 B2 | 12/2007 | Banfield et al. | |
| 7,415,426 B2 | 8/2008 | Williams et al. | |
| 7,426,480 B2 | 9/2008 | Granger et al. | |
| 7,630,908 B1* | 12/2009 | Amrien | G06F 19/322 |
| | | | 235/487 |
| 7,734,483 B1 | 6/2010 | Smith et al. | |
| 7,957,983 B2 | 6/2011 | Hoffman et al. | |
| 8,032,393 B2 | 10/2011 | Palazzolo et al. | |
| 8,036,913 B1 | 10/2011 | Pinsonneault et al. | |
| 2002/0002495 A1 | 1/2002 | Ullman | |
| 2002/0087583 A1 | 7/2002 | Morgan et al. | |
| 2002/0111832 A1 | 8/2002 | Judge | |
| 2002/0165736 A1 | 11/2002 | Tolle et al. | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0074218 A1 | 4/2003 | Liff et al. | |
| 2003/0125986 A1 | 7/2003 | Collosi | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0006490 A1* | 1/2004 | Gingrich | G06F 19/328 |
| | | | 705/2 |
| 2004/0039599 A1 | 2/2004 | Fralic | |
| 2004/0054657 A1 | 3/2004 | Takeyama | |
| 2004/0073457 A1 | 4/2004 | Kalies et al. | |
| 2004/0078234 A1 | 4/2004 | Tallal, Jr. et al. | |
| 2004/0107117 A1 | 6/2004 | Denny | |
| 2004/0111277 A1 | 6/2004 | Pearson et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0249745 A1 | 12/2004 | Baaren | |
| 2005/0015280 A1 | 1/2005 | Gabel et al. | |
| 2005/0033610 A1 | 1/2005 | Cunningham | |
| 2005/0060201 A1 | 3/2005 | Connely, III et al. | |
| 2005/0086081 A1 | 4/2005 | Brock-Fisher | |
| 2005/0090425 A1 | 4/2005 | Reardan et al. | |
| 2005/0102169 A1 | 5/2005 | Wilson | |
| 2005/0154627 A1 | 7/2005 | Zuzek et al. | |
| 2005/0171815 A1 | 8/2005 | Vanderveen | |
| 2005/0187790 A1 | 8/2005 | Lapsker | |
| 2005/0187793 A1 | 8/2005 | Myles | |
| 2005/0187821 A1 | 8/2005 | Lapsker | |
| 2005/0197862 A1 | 9/2005 | Paterson et al. | |
| 2005/0240442 A1 | 10/2005 | Lapsker | |
| 2005/0240473 A1 | 10/2005 | Ayers, Jr. et al. | |
| 2005/0288972 A1 | 12/2005 | Marvin et al. | |
| 2006/0015518 A1 | 1/2006 | Eletreby et al. | |
| 2006/0020514 A1 | 1/2006 | Yered | |
| 2006/0026041 A1 | 2/2006 | Ullman | |
| 2006/0149587 A1 | 7/2006 | Hill, Sr. et al. | |
| 2006/0149784 A1 | 7/2006 | Tholl et al. | |
| 2006/0184391 A1 | 8/2006 | Barre et al. | |
| 2006/0224415 A1 | 10/2006 | Hudson et al. | |
| 2006/0229915 A1 | 10/2006 | Kosinski et al. | |
| 2006/0259363 A1 | 11/2006 | Jhetam et al. | |
| 2006/0271398 A1 | 11/2006 | Belcastro | |
| 2006/0271402 A1 | 11/2006 | Rowe et al. | |
| 2006/0287886 A1 | 12/2006 | Kitazawa | |
| 2007/0005402 A1 | 1/2007 | Kennedy et al. | |
| 2007/0050209 A1 | 3/2007 | Yered | |
| 2007/0088576 A1 | 4/2007 | de Beus et al. | |
| 2007/0097792 A1 | 5/2007 | Burrows et al. | |
| 2007/0124177 A1 | 5/2007 | Engleson et al. | |
| 2007/0136100 A1 | 6/2007 | Daugherty et al. | |
| 2007/0174092 A1 | 7/2007 | Lara et al. | |
| 2007/0179957 A1 | 8/2007 | Gibson et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2009/0164376 A1* | 6/2009 | Guthrie | G06Q 50/22 |
| | | | 705/50 |
| 2011/0161109 A1* | 6/2011 | Pinsonneault | G06Q 50/22 |
| | | | 705/3 |

(56) References Cited

U.S. PATENT DOCUMENTS

| | | | |
|---|---|---|---|
| 2011/0196700 A1* | 8/2011 | Sekura | A61B 5/411 705/2 |
| 2013/0311205 A1 | 11/2013 | Creswell et al. | |
| 2015/0269695 A1 | 9/2015 | Pinsonneault et al. | |

FOREIGN PATENT DOCUMENTS

| | | |
|---|---|---|
| WO | 2000039737 | 7/2000 |
| WO | 2007025295 | 3/2007 |

OTHER PUBLICATIONS

Sampson, R.J., Taking Control of Health Care Costs, Best's Review—Life Health Insurance Edition, Nov. 1983, vol. 84, Issue 7, USA; Abstract only.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Anonymous, TechRx Announces Successful Beta Deployment of T-Rex. PR Newswire. May 13, 2002.

Poston, J. W., Loh, E. A., & Dunham, W. (1999). The medication use study: A large-scale controlled evaluation of the effects of the vital interests program on adherence to medication regimens. CPJ. Canadian Pharmaceutical Journal, 131 (1 0), 30-38. Retrieved from http://search.proquest.com/docview/221172694?accountid=14753.

Non-Final Office Action for U.S. Appl. No. 12/650,759 dated Jan. 27, 2012.

Final Office Action for U.S. Appl. No. 12/650,759 dated Jul. 17, 2012.

Non-Final Office Action for U.S. Appl. No. 12/650,759 dated Nov. 12, 2013.

Notice of Allowance for U.S. Appl. No. 12/650,759 dated Apr. 14, 2014.

Notice of Withdrawal from Issue Branch for U.S. Appl. No. 12/650,759 dated Jul. 30, 2014.

Non-Final Office Action for U.S. Appl. No. 12/650,759 dated Aug. 5, 2014.

Non-Final Office Action for U.S. Appl. No. 13/833,698 dated Jan. 29, 2015.

Final Office Action for U.S. Appl. No. 12/650,759 dated Feb. 9, 2015.

Non-final Office Action for U.S. Appl. No. 13/833,929 dated Feb. 13, 2015.

Final Office Action for U.S. Appl. No. 13/833,698 dated Jul. 30, 2015.

Non-final Office Action for U.S. Appl. No. 12/650,759 dated Aug. 21, 2015.

Final Office Action for U.S. Appl. No. 13/833,929 dated Oct. 8, 2015.

Office Action for Canadian Application No. 2,723,350 dated Feb. 21, 2018, 4 pages.

Office Action for U.S. Appl. No. 15/084,019 dated Feb. 15, 2019.
Office Action for U.S. Appl. No. 15/084,019 dated Jul. 27, 2018.
Office Action for U.S. Appl. No. 15/084,019 dated Jun. 24, 2019.

\* cited by examiner

SYSTEMS AND METHODS FOR DETERMINING PATIENT ADHERENCE TO A PRESCRIBED MEDICATION PROTOCOL

TECHNICAL FIELD

Aspects of the disclosure relate generally to a determination of patient adherence to medication protocols, and more particularly, to systems and methods for determining a patient adherence level to a prescribed medication protocol by monitoring healthcare transactions associated with the patient.

BACKGROUND

Physicians and other medical personnel evaluate patients to determine any adverse health conditions that the patient may have. Upon determination, the physician or other authorized prescriber of medication may prescribe one or more medications or services in an attempt to correct the patient's adverse health conditions. The prescription will typically include a protocol for how much and how often the patient should be taking each medication or receiving each type of service. Once the medications and/or services are prescribed and the patient leaves the physician's office, it is up to the patient to follow the prescribed medication protocol. In order for the physician to determine if the patient is properly following the medication protocol, the physician must question the patient during subsequent visits. Unfortunately, patients, at times, may choose to provide inaccurate information to the physician by overstating their adherence to the medication protocol. This can lead the physician to incorrectly evaluate the effectiveness of the medications or services that are being prescribed to the patient.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1:
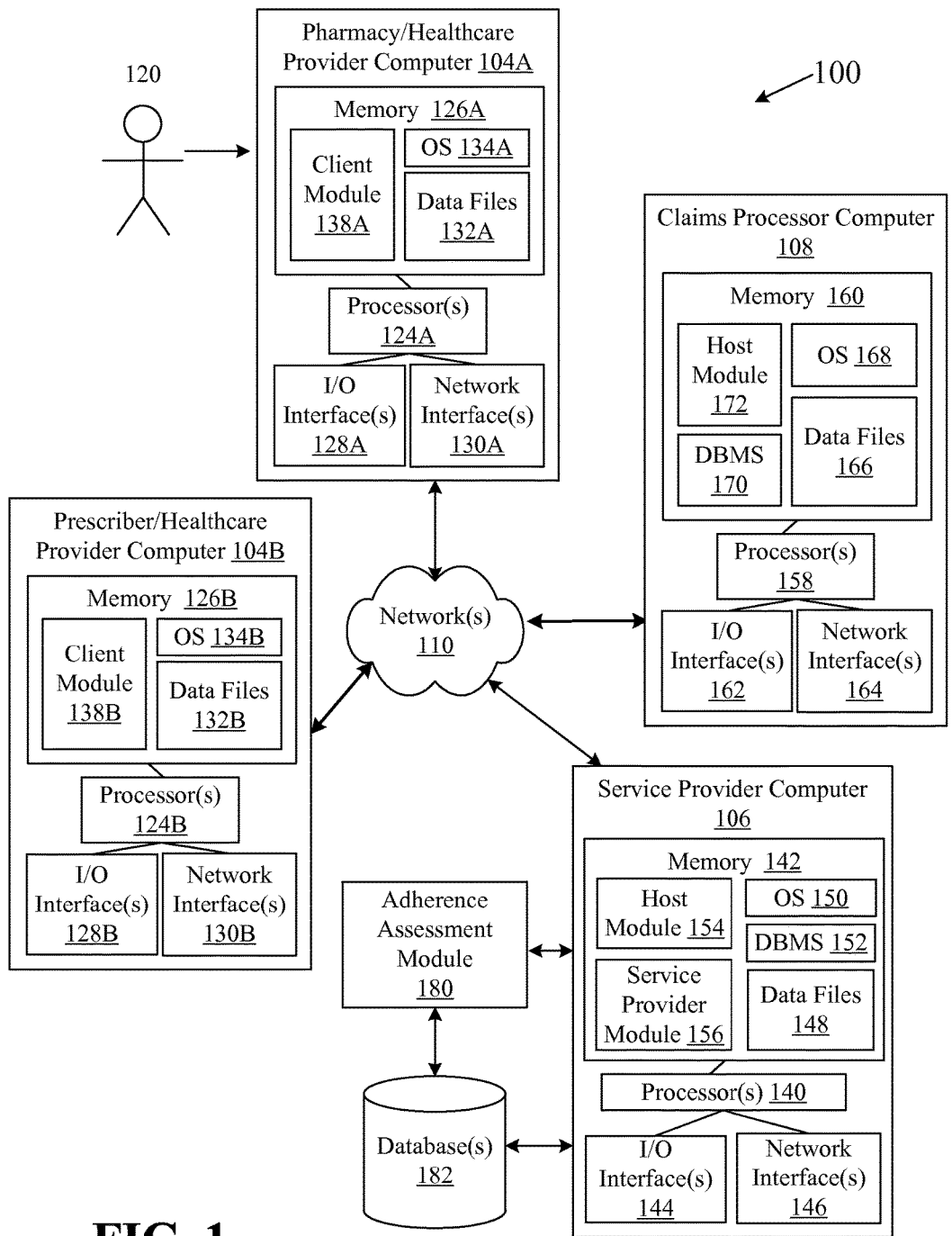
FIG. 1 illustrates an example overview of a system that facilitates determining patient adherence to a prescribed medication protocol, according to one exemplary embodiment of the disclosure.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods that facilitate the determination of patient adherence to a prescribed medication protocol, as part of the processing of the healthcare transaction in real-time or near real-time. For example, a physician or other prescriber (e.g., nurse, physician's assistant, hospital, doctor's office, or any other person permitted to prescribe a medication) can electronically transmit an e-prescription transaction (e.g., electronic prescription order transaction, e-script, or e-prescription) to a service provider computer. The service provider computer can evaluate the e-prescription transaction to determine if it is one to be used for patient adherence. For example the transaction can be evaluated to determine if the patient and/or medication match patients and medications for which adherence evaluation is desired. If the e-prescription transaction data is to be used for patient adherence, all or a portion of the data in the transaction can be stored for subsequent comparison and the transaction can be forwarded by the service provider computer to a pharmacy computer for filling of the prescription identified in the transaction.

A pharmacy or another healthcare provider can transmit a healthcare claim transaction for adjudication by a claims processor, via a healthcare provider computer, to a service provider computer. The healthcare claim transaction can be for a prescribed medication, for a patient and can be generated in response to receipt of a prescription (electronic or otherwise) for the patient. The healthcare claim transaction can be received by the service provider computer and forwarded to a claims processor computer associated with a claims processor for adjudication. The adjudicated healthcare claim transaction response can be received by the service provider computer, which can determine if the transaction was approved/paid or denied. If approved/paid, the service provider computer can determine, based on information in the transaction, if the patient and, optionally the requested medication, match stored patient data, and optionally stored medication data, for an e-prescription transaction submitted within a predetermined amount of time of a service date for the healthcare claim transaction. The service provider computer can further determine if the healthcare claim transaction is for a refill of the requested medication, and if so, can determine patient adherence based on the refill timing for the requested medication. The service provider computer can generate a prescription fill status notification and can transmit the prescription fill status notification to the physician that prescribed the medication. The notification can include a notice that the patient has filled the prescription and can also include an adherence level for the patient if one is determined.

System Overview

FIG. 1 illustrates an example system 100 supporting healthcare transactions, electronic prescription ordering activities, prescription billing activities, and patient coverage eligibility verifications according to one example embodiment. The exemplary system 100 facilitates determining patient adherence to a prescribed medication protocol as part of the processing of the healthcare transaction, including, but not limited to, an eligibility verification request, predetermination of benefits transaction, healthcare claim transaction, prescription claim or billing request, healthcare order transaction, or e-prescription transaction (e.g., electronic prescription order transaction, e-script, or e-prescription), and will now be described illustratively with respect to FIG. 1. As shown in FIG. 1, the system 100 may include at least one healthcare provider computer 104, at least one service provider computer 106, and at least one claims processor computer 108. As shown in FIG. 1, multiple healthcare provider computers 104A and 104B are presented by way of example and may be referred to individually or collectively as "healthcare provider computer 104" hereinafter. Alternatively, each of the pharmacy/healthcare provider computer 104A and prescriber/healthcare provider computer 104B may be specifically discussed with reference to designations on FIG. 1.

As desired, each of the healthcare provider computers 104A and 104B, service provider computer 106, and/or claims processor computer 108 may include one or more processing devices that may be configured for accessing and reading associated computer-readable media having stored thereon data and/or computer-executable instructions for implementing various methods, including those described herein.

Additionally, in certain exemplary embodiments, the service provider computer 106 may be in communication with one or more adherence assessment modules 180, which may access and/or be in communication with one or more suitable data storage devices, such as database 182. The adherence assessment module 180 may receive healthcare transactions or all or a portion of the data from healthcare transactions from the service provider computer 106. Upon receipt of the healthcare transaction data, the terminal care assessment module 180 may evaluate the data to determine if the healthcare transaction is for a patient, and optionally a medication for which adherence monitoring is being provided. For e-prescription transactions (e.g., electronic prescription order transaction, e-script, or e-prescription), the adherence assessment module 180 can store all or a portion of the data in the e-prescription transaction. For healthcare claim transactions (e.g., prescription claim requests, prescription billing requests, and healthcare order transactions), the adherence assessment module 180 can compare the patient identifier, and optionally the medication identifier, to the stored patient, and optionally medication identifiers, from the e-prescription transactions to determine if a match exists. The adherence assessment module 180 can also evaluate the healthcare claim transaction to determine if the transaction is for a refill or maintenance medication, and if so, can determine the adherence level for the patient taking that particular medication. The adherence assessment module 180 can also generate a prescription fill status notification that can be sent to the prescriber of the medication for the patient in the healthcare claim transaction. The notification can take the form of a National Council for Prescription Drug Programs (NCPDP) Script transaction, an NCPDP Telecommunications transaction, HL7 transaction, an X-12 transaction or some other form of healthcare transaction. Alternatively, the notification can be sent to the prescriber via email, SMS text, MMS text, facsimile transmission, or some other form of digital communications transmission. The notification can include the patient identifier, medication identifier, the date of service for the e-prescription transaction and/or the healthcare claim transaction, and, optionally, an adherence level for the patient taking the medication. The adherence assessment module 180 can communicate the notification to the service provider computer 106 or it can transmit directly the notification to the prescriber/healthcare provider computer 104B. While FIG. 1 shows the adherence assessment module 180 as being separate from the service provider computer 106, in certain example embodiments, the adherence assessment module 180 is part of the service provider computer 106 and sending and receiving between the two are internal transmissions within the service provider computer 106. Furthermore, while FIG. 1 shows the adherence assessment module 180 as a single module, in certain example embodiments, the functions/operations discussed below with regard to the adherence assessment module 180 may be completed by multiple modules, all or a portion of which may be part of the service provider computer 106.

Generally, network devices and systems, including one or more of the healthcare provider computers 104A and 104B, service provider computer 106, adherence assessment module 180, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computers 104A and 104B, service provider computer 106, claims processor computer 108, and adherence assessment module 180 may be in communication with each other via one or more networks, such as network 110, which as described below can include one or more separate or shared private and public networks, including the Internet or a publicly switched telephone network. Each of these components—the healthcare provider computers 104A and 104B, service provider computer 106, claims processor computer 108, adherence assessment module 180, and the network 110 will now be discussed in further detail.

Each healthcare provider computer 104 may be associated with a healthcare provider, such as, for example, a pharmacy, physician's office, hospital, clinic, hospice, etc. While the exemplary healthcare provider computers 104A and 104B reference and can be located within a pharmacy (104A) and an office for a prescriber (104B) this is for example only and is not intended to be limiting in any manner. Each healthcare provider computer 104A and 104B may be any suitable processor-driven device that facilitates the processing of healthcare requests made by patients, consumers, or prescribers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain example embodiments, each healthcare provider computer 104A and 104B may be a suitable point of sale device associated with a healthcare provider. The execution of the computer-implemented instructions by either healthcare provider computer 104A and 104B may form a special purpose computer or other particular machine that is operable to facilitate the processing of healthcare requests made by patients and the communication of information associated with healthcare transactions to a service provider computer 106. Additionally, in certain example embodiments of the disclosure, the operations and/or control of each healthcare provider computer 104A and 104B may be distributed amongst several processing components.

In addition to each healthcare provider computer 104A and 104B having one or more processors 124A and 124B, each healthcare provider computer 104A and 104B may also include one or more memory devices 126A and 126B, one or more input/output ("I/O") interfaces 128A and 128B, and one or more network interfaces 130A and 130B. The memory devices 126A and 126B may be any suitable memory device, for example, caches, read-only memory devices, random access memory devices, magnetic storage devices, removable storage devices, etc. The memory devices 126A and 126B may store data, executable instructions, and/or various program modules utilized by each respective healthcare provider computer 104A and 104B, for example, data files 132A and 132B, an operating system ("OS") 134A and 134B, and/or a client module 138A and 138B, respectively. Each of the data files 132A and 132B may include any suitable data that facilitates the receipt and/or processing of healthcare requests by the respective healthcare provider computer 104A and 104B and the generation and/or processing of healthcare transactions that are communicated to the service provider computer 106. For example, the data files 132A and 132B may include, but are not limited to, healthcare information and/or contact information associated with one or more patients, information associated with the particular healthcare provider and/or the respective healthcare provider computer 104A and 104B, information associated with the service provider computer 106, information associated with one or more claims processors, and/or information associated with one or more healthcare transactions. The OS 134A and 134B may be any suitable software module that controls the general operation of the respective healthcare provider computer 104A and 104B. The OS 134A and 134B may also facilitate the execution of other software modules by the one or more respective processors 124A and 124B, for example, the client module 138A and 138B. The OS 134A and 134B may be, but is not limited to, Microsoft Windows®, Apple OSX™, Linux, Unix, or a mainframe operating system.

Each client module 138A and 138B may be, for example, an Internet browser or other suitable software, including a dedicated program, for interacting with the service provider computer 106. For example, a user 120, such as a pharmacist, pharmacy assistant, nurse practitioner, physician, nurse, or other pharmacy, hospital or physician's office employee, may utilize the respective client module 138A and 138B in preparing and providing a healthcare transaction, such as a healthcare claim transaction, prescription claim or billing request, healthcare order transaction, or e-prescription transaction (e.g., electronic prescription order transaction, e-script, or e-prescription), to the service provider computer 106 for delivery to: i) the appropriate claims processor computer 108 or other third-party for adjudication or other coverage/benefits determination, or ii) the appropriate other healthcare provider computer, such as from the prescriber/healthcare provider computer 104B to a pharmacy/healthcare provider computer 104A for dispensing of the prescribed medication. Each healthcare provider computer 104A and 104B may also utilize the respective client module 138A and 138B to retrieve or otherwise receive data, messages, or responses from the service provider computer 106 and/or other components of the system 100. For example, in certain example embodiments, the client module 138A and 138B may be utilized to receive a healthcare transaction, a rejection of the healthcare transaction, a prescription fill status notification, and/or an adjudicated response to the healthcare transaction from the service provider computer 106 as will be described below.

The one or more I/O interfaces 128A and 128B may facilitate communication between the respective healthcare provider computer 104A and 104B and one or more input/output devices, for example, one or more user interface devices, such as, a display, keypad, control panel, touch-screen display, remote control, microphone, etc., that facilitate user interaction with the particular healthcare provider computer 104A and 104B. For example, the one or more I/O interfaces 128A and 128B may facilitate entry of information associated with a healthcare transaction by an employee 120 of a healthcare provider, such as a pharmacy employee, pharmacist, physician, nurse, hospital employee, or nurse practitioner affiliated with a pharmacy, hospital, physician's office, clinic, or other similar healthcare provider. The one or more network interfaces 130A and 130B may facilitate connection of the particular healthcare provider computer 104A and 104B to one or more suitable networks, for example, the network 110 illustrated in FIG. 1. In this regard, each healthcare provider computer 104A and 104B may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the healthcare provider computers 104A and/or 104B, the adherence assessment module 180, and/or the claims processor computer 108 relating to patient adherence assessments, pharmacy benefits, billing, electronic prescription submission, and/or other healthcare transactions and/or other activities. In certain exemplary embodiments, the service provider computer 106 may be a switch/router that routes healthcare transactions and/or other healthcare requests. For example, the service provider computer 106 may route healthcare claim transactions communicated from one of the healthcare provider computers 104A and 104B to a claims processor computer 108, such as a pharmacy benefits manager (PBM), an insurer, a Medicare payor, a Medicare Part D payor, accountable care organization, or other third-party payor. In another example, the service provider computer 106 may route healthcare transactions communicated from a prescriber/healthcare provider computer 104B (or other prescriber of medication, products, and/or services) to the pharmacy/healthcare provider computer 104A.

In certain example embodiments, the service provider computer 106 may include a suitable host server, host module, or other software that facilitates the receipt of a healthcare transaction from a healthcare provider computer 104A and 104B and/or the routing of the received healthcare transaction to a claims processor computer 108 or pharmacy/healthcare provider computer 104A. Any number of healthcare provider computers 104A and 104B, adherence assessment modules 180, and/or claims processor computers 108 may be in communication with the service provider computer 106 as desired in various embodiments.

The service provider computer 106 may include any number of special purpose computers or other particular machines, application-specific circuits, microcontrollers, personal computers, minicomputers, mainframe computers, servers, networked computers, and/or other processor-driven devices. In certain example embodiments, the operations of the service provider computer 106 may be controlled by computer-executed or computer-implemented instructions that are executed by one or more processors associated with the service provider computer 106 to form a special-purpose computer or other particular machine that is operable to facilitate the receipt, routing, and/or processing of healthcare transactions. The one or more processors that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the healthcare provider computers 104A and 104B described above, the service provider computer 106 may include one or more processors 140, one or more memory devices 142, one or more input/output ("I/O") interface(s) 144, and one or more network interface(s) 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a service provider module 156, and a database management system ("DBMS") 152 to facilitate management of data files 148 and other data stored in the memory devices 142. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The service provider module 156 may be operable to perform one or more pre-edits or pre-analysis on a received healthcare transaction prior to routing or otherwise communicating the received healthcare transaction, such as a healthcare claim transaction, to a suitable claims processor computer 108 or an e-prescription transaction to a suitable pharmacy/healthcare provider computer 104A. Additionally, the service provider module 156 may be operable to perform one or more post-edits on an adjudicated reply or response that is received from a claims processor computer 108 for a healthcare transaction prior to routing the adjudicated response to one of the healthcare provider computers 104A and 104B. A wide variety of different pre-edits and/or post-edits may be performed as desired in various embodiments of the disclosure.

According to one exemplary embodiment, the data files 148 may store healthcare transaction records associated with communications received from various healthcare provider computers 104A and 104B, the adherence assessment module 180, and/or various claims processor computers 108. The data files 148 may also store any number of suitable routing tables that facilitate determining the destination of communications received from a healthcare provider computer 104A and 104B, the adherence assessment module 180, and/or the claims processor computer 108.

The exemplary data files 148 may also store records containing, for example, patient identification data, tables, schedules, or lists of patient identification data and medication identification data for patients (e.g., patient first name, patient last name, patient social security number or healthcare insurance claim number (HICN number), cardholder ID and/or person code for the patient) and medications (e.g., National Drug Code (NDC code) medication name and/or other medication identifier) for which adherence assessment is to be conducted.

The host module 154 may receive, process, and respond to requests from the client module 138 of one of the healthcare provider computers 104A and 104B, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware, or software without departing from exemplary embodiments disclosed herein.

With continued reference to the service provider computer 106, the one or more I/O interfaces 144 may facilitate communication between the service provider computer 106 and one or more input/output devices, for example, one or more user interface devices, such as a display, keypad, control panel, touch-screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

The adherence assessment module 180 of FIG. 1 represents one or more modules that can evaluate a healthcare transaction or data from a healthcare transaction to determine if the transaction is for a patient, and optionally a medication, for which adherence assessment should be completed, can complete the adherence assessment, and can generate prescription fill notifications that can be transmitted to the prescriber of the medication in the healthcare transaction, such as by sending the notification to the prescriber/healthcare provider computer 104B via the network 110. The example adherence assessment module 180 may include computer-executable instructions for receiving and processing healthcare transactions or healthcare transaction data from a service provider computer 106.

The adherence assessment module 180 may receive healthcare transactions or all or a portion of the data from healthcare transactions from the service provider computer 106. Upon receipt of the healthcare transaction data, the terminal care assessment module 180 may evaluate the data to determine if the healthcare transaction is for a patient, and optionally a medication for which adherence monitoring is being provided. For e-prescription transactions (e.g., electronic prescription order transaction, e-script, or e-prescription), the adherence assessment module 180 can store all or a portion of the data in the e-prescription transaction. For healthcare claim transactions (e.g., prescription claim requests, prescription billing requests, and healthcare order transactions), the adherence assessment module 180 can compare the patient identifier, and optionally the medication identifier, to the stored patient, and optionally medication identifiers, from the e-prescription transactions to determine if a match exists. The adherence assessment module 180 can also evaluate the healthcare claim transaction to determine if the transaction is for a refill or maintenance medication, and if so, can determine the adherence level for the patient taking that particular medication. The adherence assessment module 180 can also generate a prescription fill status notification that can be sent to the prescriber of the medication for the patient in the healthcare claim transaction. The notification can take the form of a National Council for Prescription Drug Programs (NCPDP) Script transaction, an NCPDP Telecommunications transaction, HL7 transaction, an X-12 transaction or some other form of healthcare transaction. Alternatively, the notification can be sent to the prescriber via email, SMS text, MMS text, facsimile transmission, or some other form of digital communications transmission. The notification can include the patient identifier, medication identifier, the date of service for the e-prescription transaction and/or the healthcare claim transaction, and, optionally, an adherence level for the patient taking the medication. The adherence assessment module 180 can communicate the notification to the service provider computer 106 or it can transmit directly the notification to the prescriber/healthcare provider computer 104B. While FIG. 1 shows the adherence assessment module 180 as being separate from the service provider computer 106, in certain example embodiments, the adherence assessment module 180 is part of the service provider computer 106 and sending and receiving between the two are internal transmissions within the service provider computer 106. Furthermore, while FIG. 1 shows the adherence assessment module 180 as a single module, in certain example embodiments, the functions/operations discussed below with regard to the adherence assessment module 180 may be completed by multiple modules, all or a portion of which may be part of the service provider computer 106.

As desired, the adherence assessment module 180 may include any number of special purpose computers or other particular machines, application-specific circuits, microcontrollers, personal computers, minicomputers, mainframe computers, servers, and the like. In certain exemplary embodiments, the operations of the adherence assessment module 180 may be controlled by computer-executed or computer-implemented instructions that are executed by one or more processors associated with the adherence assessment module 180 to form a special purpose computer or other particular machine that is operable to facilitate the receipt, processing, and/or storage of healthcare transactions and/or healthcare transaction data received from the service provider computer 106. The one or more processors that control the operations of the adherence assessment module 180 may be incorporated into the adherence assessment module 180 and/or in communication with the adherence assessment module 180 via one or more suitable networks, such as network 110. In certain example embodiments, the operations and/or control of the adherence assessment module 180 may be distributed amongst several processing components.

Similar to other components of the system 100, the adherence assessment module 180 may include one or more processors, one or more memory devices, one or more I/O interfaces, and one or more network interfaces. The one or more memory devices may be any suitable memory devices, for example, caches, read only memory devices, random access memory devices, magnetic storage devices, removable memory devices. The one or more memory devices may store data, executable instructions, and/or various program modules utilized by the adherence assessment module 180, for example, data files, an OS, a DBMS, and a host module. The data files may include any suitable information that is utilized by the terminal care assessment module 180 to receive, process, analyze, and/or store healthcare transaction data. The OS may be a suitable software module that controls the general operation of the particular adherence assessment module 180. The OS may also facilitate the execution of other software modules by the one or more processors, for example, the DBMS and/or the host module. The OS may be, but is not limited to, Microsoft Windows®, Apple OSX™, Linux, Unix, or a mainframe operating system. The DBMS may be a suitable software module that facilitates access and management of one or more databases, such as database 182, that are utilized to store information that is received by or utilized by the adherence assessment module 180 and/or the service provider computer 106. The host module may initiate, receive, process, analyze, store, and/or respond to requests, such as the receipt of healthcare transactions or healthcare transaction data from the host module 154 of the service provider computer 106. The adherence assessment module 180 may include additional program modules as desired. Those of ordinary skill in the art will appreciate that the adherence assessment module 180 may include alternate and/or additional components, hardware or software without departing from example embodiments disclosed herein.

The one or more I/O interfaces may facilitate communication between the adherence assessment module 180 and one or more input/output devices, for example, one or more user interface devices, such as a display, keypad, control panel, touch-screen display, remote control, microphone, etc. that facilitate user interaction with the adherence assessment module 180. The one or more network interfaces may facilitate connection of adherence assessment module 180 to one or more suitable networks, for example, the network 110 illustrated in FIG. 1. In this regard, the adherence assessment module 180 may receive healthcare transactions, healthcare transaction data, and/or other communications from the service provider computer 106. While FIG. 1 shows the adherence assessment module 180 as being separate from the service provider computer 106, in certain example embodiments, the adherence assessment module 180 is part of the service provider computer 106 and sending and receiving between the two are internal communications within the service provider computer 106.

The database(s) 182 may be operable to store information associated with various patients and/or various transactions involving adherence assessment, including, but not limited to, patient identification data, tables, schedules, or lists of patient identification data for patients for which adherence assessments are to be completed (e.g., patient first name, patient last name, patient social security number or HICN number, cardholder ID and/or person code for the patient) and, optionally, tables, schedules, or lists of medication identifiers for medications for which adherence assessments are to be completed for the listed patients (e.g., the related NDC code and/or medication name for the medication in the healthcare transaction). The patient and prescription medication data in the database 182 may then be accessed and evaluated by the adherence assessment module 180 and/or the service provider computer 106.

With continued reference to FIG. 1, the claims processor computer 108 may be any suitable processor-driven device that facilitates receiving, processing, and/or fulfilling healthcare transactions, such as healthcare claim transactions, prescription claim or billing requests, healthcare order transactions, or e-prescription transactions (e.g., electronic prescription order transactions, e-scripts, or e-prescriptions) received from the service provider computer 106. For example, the claims processor computer 108 may be a processor-driven device associated with a pharmacy benefits manager (PBM), an insurer, a government payor, a Medicare Part D payor, accountable care organization, or a claims clearinghouse. As desired, the claims processor computer 108 may include any number of special purpose computers or other particular machines, application-specific circuits, microcontrollers, personal computers, minicomputers, mainframe computers, servers, and the like.

In certain exemplary embodiments, the operations of the claims processor computer 108 may be controlled by computer-executed or computer-implemented instructions that are executed by one or more processors associated with the claims processor computer 108 to form a special-purpose computer or other particular machine that is operable to facilitate the receipt, processing, and/or fulfillment of healthcare transaction requests received from the service provider computer 106. The one or more processors that control the operations of the claims processor computer 108 may be incorporated into the claims processor computer 108 and/or in communication with the claims processor computer 108 via one or more suitable networks. In certain embodiments, the operations and/or control of the claims processor computer 108 may be distributed amongst several processing components.

Similar to other components of the system 100, the claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions, for example, patient profiles, patient insurance information, other information associated with a patient, information associated with a healthcare provider, etc. The operating system (OS) 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system.

The DBMS 170 may be a suitable software module that facilitates access and management of one or more databases that are utilized to store information that is utilized by the claims processor computer 108 in various example embodiments of the disclosure. The host module 172 may initiate, receive, process, and/or respond to requests, such as healthcare transactions or claim requests, from the host module 154 of the service provider 106. The claims processor computer 108 may include additional program modules for performing other pre-processing or post-processing methods described herein. Those of ordinary skill in the art will appreciate that the claims processor computer 108 may include alternate and/or additional components, hardware or software without departing from the example embodiments described herein.

The one or more I/O interfaces 162 may facilitate communication between the claims processor computer 108 and one or more input/output devices, for example, one or more user interface devices, such as a display, keypad, control panel, touch-screen display, remote control, microphone, etc. that facilitate user interaction with the claims processor computer 108. The one or more network interfaces 164 may facilitate connection of the claims processor computer 108 to one or more suitable networks, for example, the network 110. In this regard, the claims processor computer 108 may receive healthcare transactions and/or other communications from the service provider computer 106 and the claims processor computer 108 may communicate information associated with processing the healthcare transactions to the service provider computer 106.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computers 104A and 104B, the service provider computer 106, adherence assessment module 180, and/or the claims processor computer 108. Due to network connectivity, various methodologies, as described herein may be practiced in the context of distributed computing environments. Although the service provider computer 106 is shown for simplicity as being in communication with the healthcare provider computers 104A and 104B, the adherence assessment module 180, or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 106 may form the basis of network 110 that interconnects one or more of the healthcare provider computers 104A and 104B, the adherence assessment module 180, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 106 (or other computer) may be implemented as a specialized processing machine that includes hardware and/or software for performing the methods described herein. In addition, at least a portion of the processor and/or processing capabilities of the service provider computer 106 may be implemented as part of the claims processor computer 108 or the healthcare provider computer 104. In addition, at least a portion of the processor and/or processing capabilities of the healthcare provider computer 104, and/or the claims processor computer 108 may be implemented as part of the service provider computer 106. Accordingly, the exemplary embodiments described herein should not be construed as being limited to any particular operating environment, system architecture, or device configuration.

Operational Overview

Figure 2A:
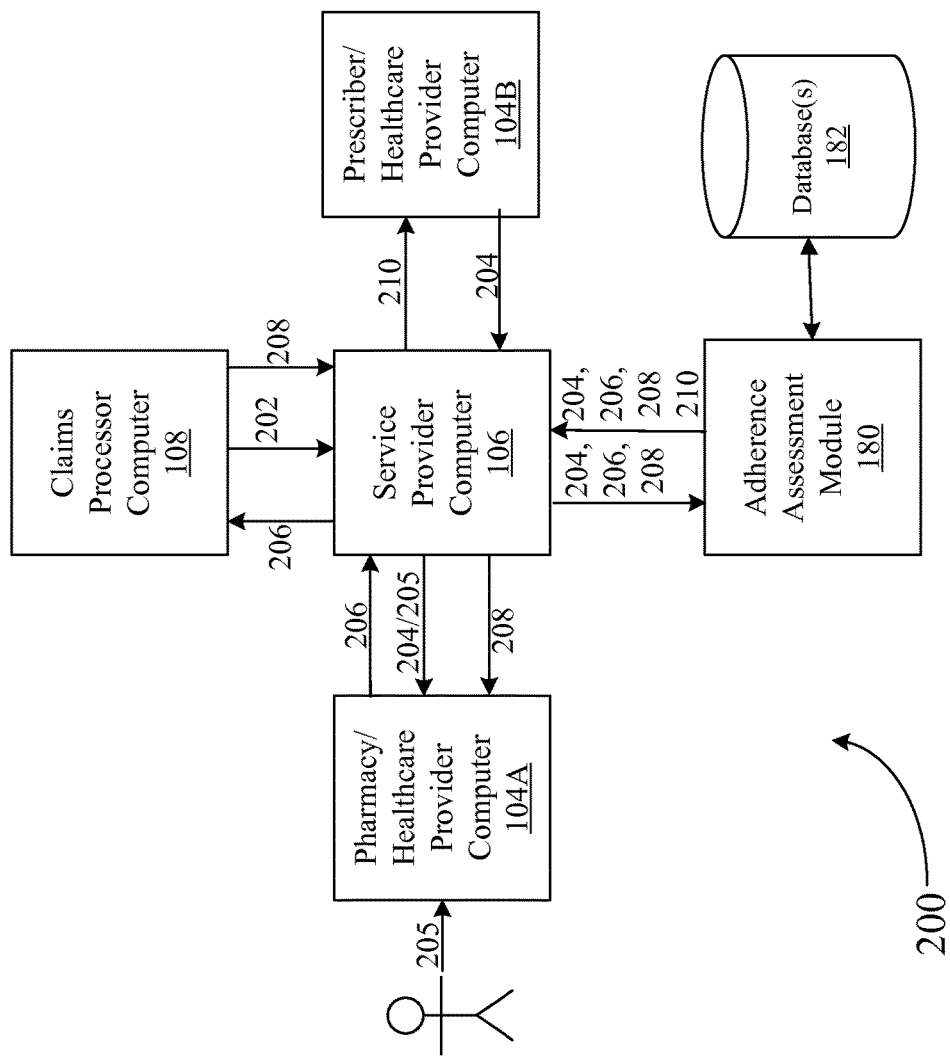
FIG. 2A is a diagram of an example data flow for evaluating healthcare transactions to determine patient adherence to a prescribed medication protocol as part of the processing of the healthcare transaction, according to one exemplary embodiment of the disclosure.
Figure 3:
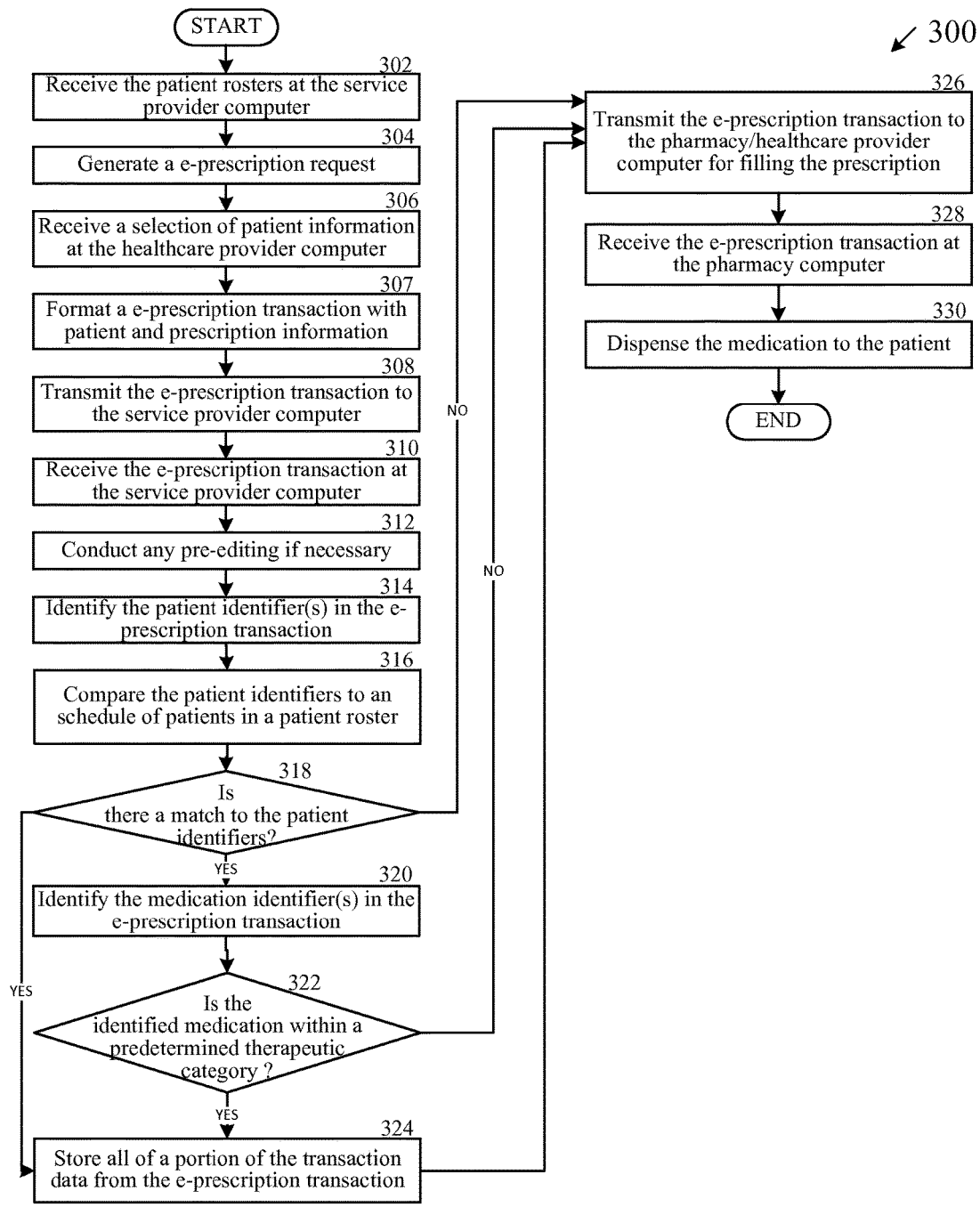
FIG. 3 is a flow chart of an example method for evaluating and storing electronic prescription data for use in determining patient adherence to a prescribed medication protocol as part of the processing of the healthcare transaction, according to one exemplary embodiment of the disclosure.

FIG. 2A is a diagram of one example data flow 200 for evaluating healthcare transactions to determine patient adherence to a prescribed medication protocol as part of the processing of the healthcare transaction through a service provider computer, such as through the service provider computer 106 illustrated in FIG. 1. FIG. 3 is a flow chart of an example method 300 for evaluating and storing electronic prescription data for use in determining patient adherence to a prescribed medication protocol as part of the processing of a healthcare transaction (such as a predetermination of benefits transaction, a healthcare claim transaction, prescription claim or billing request, healthcare order transaction, or e-prescription transaction (e.g., electronic prescription order transaction, e-script, or e-prescription)) for that patient through a service provider computer 106, in accordance with one exemplary embodiment. All or a portion of the steps in the exemplary method 300, described below, may be performed by a suitable service provider computer 106 and/or adherence assessment module 180.

The exemplary method 300 will be described with reference to a prescriber (e.g., physician, nurse, nurse practitioner, hospital or any other person permitted to prescribe medications to patients) as one healthcare provider (and accordingly a prescriber computer as the first healthcare provider computer 104B and a pharmacy as another healthcare provider (and accordingly a pharmacy computer as another healthcare provider computer 104A). However, this is only for purposes of example as other healthcare providers could be substituted for, and should each be individually read as being a part of this method. As such, where the discussion of the methods below and the drawings state a prescriber and/or a pharmacy, any other healthcare provider could be substituted, such as a physician, hospital, physician's office, clinic, or healthcare center.

In addition, the exemplary method 300 will be described with reference to a e-prescription transaction; however, this also is only for purposes of example as other healthcare transactions, which may include, for example, a predetermination of benefits transaction, the healthcare claim transaction, prescription claim or billing request, healthcare order transaction, or e-prescription transaction (e.g., electronic prescription order transaction, e-script, or e-prescription) could be substituted for the e-prescription transaction and each form of healthcare transaction should each individually be read as being used in the method described below.

Referring now to FIGS. 1, 2A, and 3, the exemplary method 300 begins at the START step and proceeds to step 302, where the service provider computer 106 and/or the adherence assessment module 180 can receive patient roster 202 from, for example, one or more claims processor computers 108 or the accountability care organization, insurance provider, pharmacy benefits manager, Medicare Part D provider or other entity represented by the claims processor associated with the claims processor computer 108. In one example embodiment, the patient roster 202 can include a table, list, or schedule of patients and/or patient identifiers (e.g., patient first name, patient last name, patient date of birth, patient gender, patient address, patient social security number, patient HICN, insurance cardholder name, and/or insurance person code) that identifies patients for which the accountability care organization, PBM, insurer, claims processor, or other payor wants adherence assessments to be completed. In addition, the patient roster 202 can include a table, list, or schedule of medications and/or therapeutic categories for which the accountability care organization, PBM, insurer, claims processor, or other payor wants adherence assessments to be completed for the particular patient. While the example embodiment shows one patient roster being received, in certain example embodiments, multiple patient rosters can be received by the service provider computer 106 from accountability care organizations, PBMs, insurers, claims processors, and/or other medical claims payors and can be received via multiple claims processor computers 108 or directly from the payors. The patient rosters 202 can be received electronically or via paper and entered into an electronic file for the database 182 or data files 148. Further, while the example embodiment shows the patient rosters 202 being received once, this is for example only, as these rosters 202 can be received and updated daily, weekly, monthly, quarterly, annually, or any other constant or variable time period.

In step 304, a prescriber, such as a physician, physician's assistant, nurse or any other person permitted to prescribe medication, can generate an e-prescription transaction at the prescriber/healthcare provider computer 104B. The physician, for example, determines the patient's name and accesses the prescriber/healthcare provider computer 104B, which receives a selection of patient information from the prescriber via the I/O interface 128B in step 306. For example, the physician accesses the prescriber/healthcare provider computer 104B and accesses a database of patient information, which may be stored in memory 126B or in another database either local or remote from the prescriber/healthcare provider computer 104B. The physician can then select the name or other patient identification information in the patient information database that matches the name or other identification information of the patient.

In step 307, an e-prescription transaction 204 is formatted at the prescriber/healthcare provider computer 104B. In certain exemplary embodiments, the prescriber/healthcare provider computer 104B formats the e-prescription transaction 204 with patient information (e.g., patient identifiers), pharmacy identifiers, and medication information (e.g., medication identifiers). The information can be input into the e-prescription transaction 204 by the physician via the I/O interface 128B or automatically retrieved and entered by the prescriber/healthcare provider computer 104B and, in certain situations, can be based at least in part on historical transaction information for the patient in the data files 132B or a database communicably coupled to the prescriber/healthcare provider computer 104B. According to one example embodiment, the e-prescription transaction 204 may be formatted in accordance with a version of the NCPDP Script Standard, although other standards, such as X-12 Standard, Health Law 7 (HL7) Standard, or NCPDP Telecommunication Standard may be utilized as well.

As discussed above, the e-prescription transaction 204 may include a pharmacy identifier for identifying a particular pharmacy/healthcare provider computer 104A as a destination for the e-prescription transaction 204. In addition, the e-prescription transaction 204 may also include information relating to the patient, payor, prescriber, healthcare provider, and/or the requested medication. As an example, the e-prescription transaction 204 may include one or more of the following information:

Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Store Address, Chain Identifier, etc.)
Pharmacy or other Healthcare Provider ID (e.g. NPI code)
Claim Information
Medication information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Number of Refills Authorized
Prescription Instructions
Substitution of Medication Options
One or more NCPDP Message Fields
Date of Service.

The e-prescription transaction 204 can be used to transmit a prescription from a prescriber to a pharmacy for filling of the prescription. The prescriber/healthcare provider computer 104B can transmit the e-prescription transaction 204 to the service provider computer 106 in step 308. In step 310, the service provider computer 106 receives the e-prescription transaction 204. For example, the e-prescription transaction 204 can be transmitted by the prescriber/healthcare provider computer 104B to the service provider computer 106 through the network 110. The service provider computer 106 conducts any pre-editing, if necessary, on the e-prescription transaction 204 in step 312. The pre-edits may include verifying, adding, and/or editing information included in the e-prescription transaction 204 prior to it being communicated to a pharmacy/healthcare provider computer 104A. For example, the service provider computer 106 can parse the e-prescription transaction 204 to determine/edit the financial fields, the service code, the quantity dispensed, and or the patient age.

In step 314, the one or more patient identifiers in the e-prescription transaction 204 can be identified. For example, the patient identifiers can be the Cardholder Name (e.g., cardholder first name and last name (which can be different from the patient's first and last name) on the patient's insurance card) and Cardholder ID (e.g., person code on the patient's insurance card). In addition, or in the alternative, the patient identifiers can be one or more of the patient first name, patient last name, patient gender, patient date of birth, patient address, patient contact information (e.g., phone number or email address), patient social security number, and/or patient HICN. In one example embodiment, the one or more patient identifiers can be identified by the adherence assessment module 180 or another portion of the service provider computer 106 based on a review of the data in the e-prescription transaction 204. In step 316, the identified one or more patient identifiers can be compared to a table, schedule, or list of patient identifiers for patients to receive adherence assessment evaluations. In certain example embodiments, the list of patient identifiers for patients receiving adherence assessment evaluations can be based on the patient record received from the accountability care organization, claims processor, or other payor, as discussed in step 302. In one example embodiment, the comparison can be made by the adherence assessment module 180 or another portion of the service provider computer 106.

In step 318, an inquiry is conducted to determine if the identified one or more patient identifiers matches one or more of the patient identifiers in the table, schedule, or list of identifiers for patients receiving adherence assessment evaluations. In one example embodiment, the adherence assessment module 180 or another portion of the service provider computer 106 can determine if a match exists. If the identified one or more patient identifiers does not match a patient identifier for a patient receiving adherence assessment evaluations, the NO branch can be followed to step 326. If there is a match, the YES branch is followed optionally to step 320 or 324.

In step 320, the identifier for the medication being requested in the e-prescription transaction 204 (hereinafter, the medication identifier) can be identified. For example, the medication identifier can be the NDC code or RxNorm number for the medication. In addition, or in the alternative, the medication identifier can be the name of the medication. In one example embodiment, the medication identifier can be identified by the adherence assessment module 180 or another portion of the service provider computer 106 based on a review of the data in a predetermined field in the e-prescription transaction 204.

In step 322, an inquiry is conducted to determine if the identified medication is within a predetermined therapeutic category. For example, the therapeutic categories of interest for adherence assessment can include, but are not limited to, medications for the treatment of hypertension, diabetes, and cholesterol. For example, the therapeutic categories can be presented as categories and the service provider computer 106 or the adherence assessment module 180 can determine the medication identifiers for medications that fall within each therapeutic category and whether the medication identifier in the e-prescription transaction 204 matches any of those medication identifiers. Alternatively, the medication identifiers can be provided for each therapeutic category, such as in the patient roster or similar file provided by the payor and the service provider computer 106 or adherence assessment module 180 can determine if the medication identifier in the e-prescription transaction 204 matches at least one of the medication identifiers in the therapeutic categories. In another alternative, instead of therapeutic categories, medication identifiers can be provided, irrespective of therapeutic category, such as in the patient roster or similar file, and the service provider computer 106 or adherence assessment module 180 can determine if the medication identifier in the e-prescription transaction 204 matches at least one of the medication identifiers. If the medication identifier from the e-prescription transaction 204 is within one of the predetermined therapeutic categories or otherwise matches medication identifiers for medication to receive adherence assessment evaluations, then the YES branch can be followed to step 324. Otherwise, if the medication identifier does not match or is not included in the therapeutic category, the NO branch is followed to step 326.

In step 324, information from the e-prescription transaction 204 can be stored in, for example, the database 182 or the data files 148. For example, the adherence assessment module 180 or another portion of the service provider computer 106 can store the prescription number, the medication identifier, the one or more patient identifiers, the pharmacy identifier, the days' supply, the medication quantity, the number of refills, and the claims processor identifier.

The service provider computer 106 can transmit the e-prescription transaction 204 to the pharmacy/healthcare provider computer 104A in step 326. For example, the e-prescription transaction 204 can be transmitted from the service provider computer 106 to the pharmacy/healthcare provider computer 104A via the network 110. The pharmacy/healthcare provider computer 104A receives the e-prescription transaction 204 in step 328. In step 330, the pharmacy, such as a pharmacist or other pharmacy employee, can dispense the medication to the patient based on information in the e-prescription transaction 204. The dispensing process can include submitting a healthcare claim transaction to a claims processor computer 108 via the service provider computer 106 in a manner the same as or similar to that described below with reference to FIG. 4. The process then continues to the END step.

Figure 4:
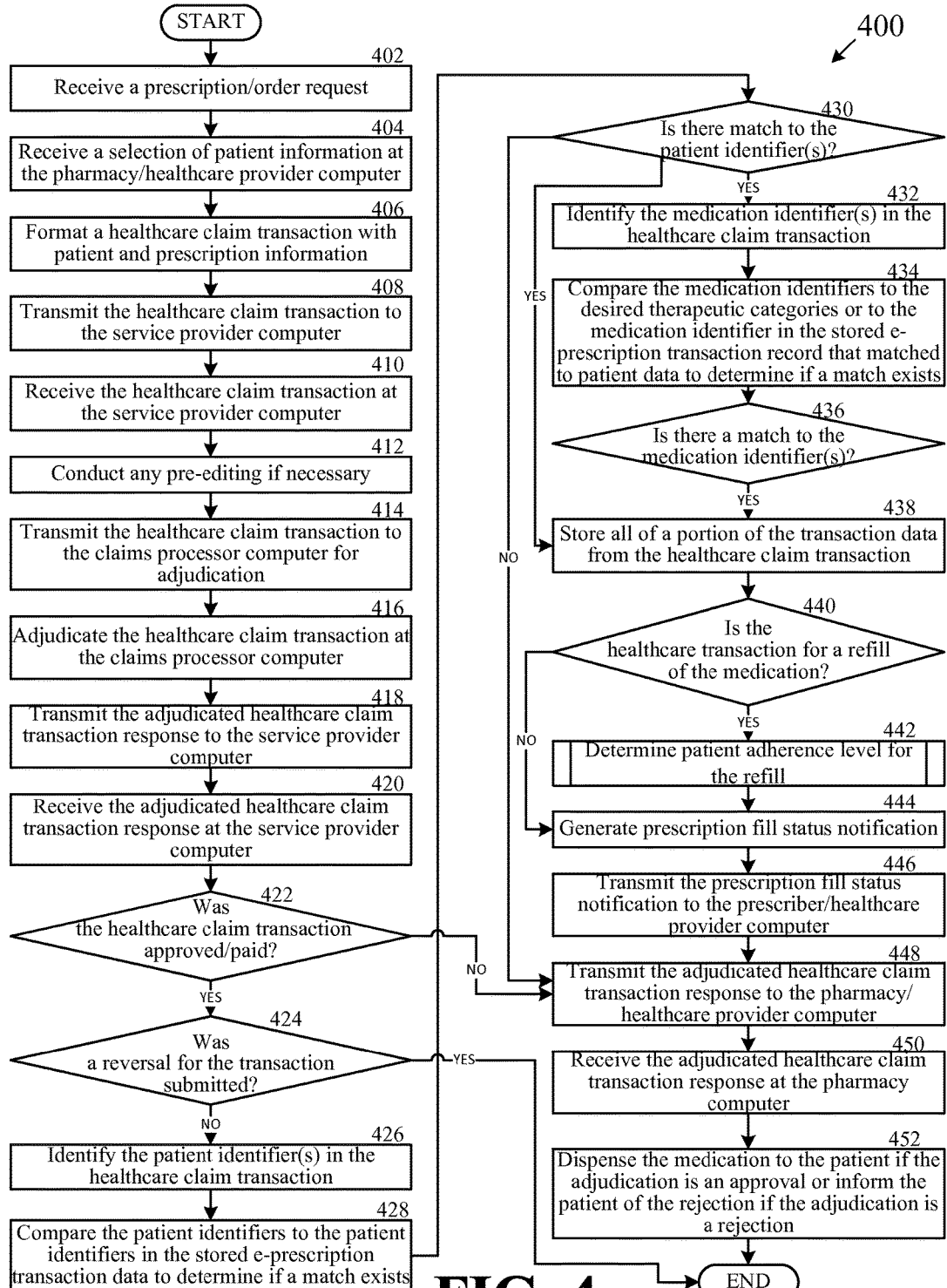
FIG. 4 is a flow chart of an example method for determining patient adherence to a prescribed medication protocol as part of the processing of the healthcare transaction, according to one exemplary embodiment of the disclosure.

FIG. 4 is a flow chart of an example method 400 for determining patient adherence to a prescribed medication protocol as part of the processing of a healthcare transaction (such as a predetermination of benefits transaction, a healthcare claim transaction, prescription claim or billing request, healthcare order transaction, or e-prescription transaction (e.g., electronic prescription order transaction, e-script, or e-prescription)) for that patient through a service provider computer, in accordance with one exemplary embodiment. All or a portion of the steps in the exemplary method 400, described below, may be performed by a suitable service provider computer 106 and/or adherence assessment module 180. The exemplary method 400 will be described with reference to a pharmacy as the healthcare provider (and accordingly a pharmacy computer as the healthcare provider computer 104A); however, this is only for purposes of example as other healthcare providers could be substituted for, and should each be individually read as being a part of each of these methods. As such, where the discussion of the methods below and the drawings state a pharmacy, any other healthcare provider could be substituted, such as a physician, hospital, physician's office, clinic, or healthcare center.

In addition, the exemplary method 400 will be described with reference to a healthcare claim transaction; however, this also is only for purposes of example as other healthcare transactions, which may include, for example, a predetermination of benefits transaction, the healthcare claim transaction, prescription claim or billing request, healthcare order transaction, or e-prescription transaction (e.g., electronic prescription order transaction, e-script, or e-prescription) could be substituted for the healthcare claim transaction and each form of healthcare transaction should each individually be read as being used in the method described below.

Referring now to FIGS. 1, 2A, and 4, the exemplary method 400 begins at the START step and proceeds to step 302, where a prescription/order request 205 is received. In one example embodiment, the prescription/order request 205 is received by a pharmacist at a pharmacy. The prescription/order request 205 may be received from a patient, another healthcare provider prescribing a medication or service (e.g., physician, clinic, physician's office, hospital, etc.), by phone, via the Internet, via an e-prescription transaction 204 or by way of an electronic system order. For example, the prescription 205 may be received by the patient from a prescriber of the medication, such as a doctor, dentist, nurse, physician's assistant, or any other person authorized to prescribe medications, products, and/or services for a patient. The patient may go to the location of the pharmacy and physically hand the prescription request 205 to the pharmacist or make a request via a web portal communicably coupled to the pharmacy/healthcare provider computer 104A or an IVR communicably coupled or otherwise providing order data to the pharmacy/healthcare provider computer 104A. The pharmacist determines the patient's name and accesses the pharmacy/healthcare provider computer 104A, which receives a selection of patient information from the pharmacist via the I/O interface 128A in step 404. For example, the pharmacist accesses the pharmacy/healthcare provider computer 104A and accesses a database of patient information, which may be stored in memory 126A or in another database either local or remote from the pharmacy/healthcare provider computer 104A. The pharmacist can then select the name or other patient identification information in the patient information database that matches the name or other identification information of the patient.

In step 406, a healthcare claim transaction 206 is generated and/or formatted at the pharmacy/healthcare provider computer 104A. In certain exemplary embodiments, the pharmacy/healthcare provider computer 104A formats the healthcare claim transaction 206 with patient information (e.g., patient identifiers), Payor ID/routing information (e.g., claims processor identifiers), and medication information (e.g., medication identifiers). The information can be input into the healthcare claim transaction 206 by the pharmacist via the I/O interface 128A or automatically retrieved and entered by the pharmacy/healthcare provider computer 104A and, in certain situations, can be based at least in part on historical transaction information for the patient in the data files 132A or a database communicably coupled to the pharmacy/healthcare provider computer 104A. According to one example embodiment, the healthcare claim transaction 206 may be formatted in accordance with a version of the National Council for Prescription Drug Programs (NCPDP) Telecommunication Standard, although other standards, such as X-12 Standard, Health Law 7 (HL7) Standard, or NCPDP Script Standard may be utilized as well.

As discussed above, the healthcare claim transaction 206 may include a BIN Number, a BIN Number and PCN, and/or a BIN Number and Group ID for identifying a particular claims processor computer (e.g., PBM, payor, healthcare insurance company, Medicare or other government healthcare insurance payor, Medicare Part D provider, etc.), such as the claims processor computer 108, as a destination for the healthcare claim transaction 206. In addition, the healthcare claim transaction 206 may also include information relating to the patient, payor, prescriber, healthcare provider, and/or the requested medication. As an example, the healthcare claim transaction 206 may include one or more of the following information:

Payor ID/Routing Information
BIN Number, BIN Number and PCN and/or BIN Number and Group ID, that designates a destination payor of the healthcare claim transaction 206
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Date of Service.

The healthcare claim transaction 206 can be used to determine if the claims processor associated with the claims processor computer 108 approves or rejects payment coverage for medication being requested in the healthcare claim transaction 206 and, if approved, the amount the claims processor will cover (or pay) for the medication being requested and how much the patient co-pay amount will be.

The pharmacy/healthcare provider computer 104A can transmit the first healthcare claim transaction 206 to the service provider computer 106 in step 408. In step 410, the service provider computer 106 receives the healthcare claim transaction 206. For example, the healthcare claim transaction 206 can be transmitted by the pharmacy/healthcare provider computer 104A to the service provider computer 106 through the network 110. The service provider computer 106 conducts any pre-editing, if necessary, on the healthcare claim transaction 206 in step 412. The pre-edits may include verifying, adding, and/or editing information included in the healthcare claim transaction 206 prior to it being communicated to a claims processor computer 108. For example, the service provider computer 106 can parse the healthcare claim transaction 206 to determine/edit the financial fields, the service code, the quantity dispensed, and or the patient age.

The service provider computer 106 can transmit the healthcare claim transaction 206 to the claims processor computer 108 in step 414. For example, the healthcare claim transaction 206 can be transmitted from the service provider computer 106 to the claims processor computer 108 via the network 110. The claims processor computer 108 receives and adjudicates the healthcare claim transaction 206 in step 416 to determine if the patient has coverage, to determine to what extent the patient's coverage covers the requested medication identified in the transaction 206 and to generate an adjudication 208 as to whether the transaction 206 is approved or rejected. Example adjudications 208 can include, but are not limited to, accepted, approved, paid, captured, denied, and denied with request for additional information and resubmission. In certain exemplary embodiments, the adjudication 208 can be input into a field of the healthcare claim transaction 206 that is recognized by the service provider computer 106 and/or the pharmacy/healthcare provider computer 104A. Typically, if the transaction 206 is approved, the adjudicated response 208 provides the amount of the cost of the medication, product, or service that will be covered by the claims processor associated with the claims processor computer 108 and the patient co-pay amount and if rejected, the adjudicated response 208 provides the reason for the rejection (e.g., patient not covered, Cardholder ID submitted in the transaction is inactive, prior authorization required, medication not covered, etc.), such as in the form of a reject code. In step 418, the claims processor computer 108 transmits the adjudicated healthcare claim transaction response 208 to the service provider computer 106 via, for example, the network 110.

The service provider computer 106 receives the adjudicated healthcare claim transaction response 208 from the claims processor computer 108 in step 420. In step 422, an inquiry is conducted to determine if the adjudication 208 for the healthcare claim transaction 206 was approved/paid. In one example embodiment, the determination can be made by the service provider module 156 or another portion of the service provider computer 106. For example, the service provider module 156 can parse the adjudicated response to the healthcare claim transaction 208 and identify the adjudication code in the adjudication field of the response 208. The service provider module 156 can then compare the adjudication code to a schedule of adjudication codes to determine the adjudication in the adjudicated response 208. If the adjudication is approved/paid, the YES branch is followed to step 422. If the adjudication is a rejection of the transaction 206, then the NO branch is followed to step 448.

In step 424, an inquiry is conducted to determine if a reversal transaction for the healthcare claim transaction 206 has been received. In one exemplary embodiment, the determination can be made by the service provider module 156 or another portion of the service provider computer 106. For example, the service provider module can compare the prescription number of other data in the reversal transaction to the prescription number or other data in the healthcare claim transaction 206 to determine if a match exists. In certain example embodiments, the service provider computer 106 may only wait a predetermined amount of time to determine if a reversal transaction has been received. For example, the predetermined amount of time can be any amount between 1 second and 1 day and preferably less than 1 hour. If the service provider module 156 determines that a reversal transaction has not been submitted, then the NO branch is followed to step 426. On the other hand, if the module 156 determines that a reversal transaction has been submitted, then the NO branch is followed to the END step and the reversal transaction is handled is a standard manner outside of this method. While the reversal inquiry is being shown as occurring prior to sending the adjudicated response 208 to the pharmacy/healthcare provider computer 104A, in other example embodiments, the reversal inquiry of step 424 can occur after the transmission of the adjudicated response 208 to the pharmacy/healthcare provider computer 104A discussed in step 448.

In step 426, the one or more patient identifiers in the healthcare claim transaction 206 or adjudicated response 208 can be identified. For example, the patient identifiers can be the Cardholder Name (e.g., cardholder first name and last name on the patient's insurance card) and Cardholder ID (e.g., person code on the patient's insurance card). In addition, or in the alternative, the patient identifiers can be one or more of the patient first name, patient last name, patient gender, patient date of birth, patient address, patient contact information (e.g., phone number or email address), patient social security number, and/or patient HICN. In one example embodiment, the one or more patient identifiers can be identified by the adherence assessment module 180 or another portion of the service provider computer 106 based on a review of the data in the healthcare claim transaction 206 or adjudicated response 208. In step 428, the identified one or more patient identifiers can be compared to stored patient identifiers for e-prescription transactions 204 for patients that are to receive adherence assessment evaluations to determine if a match exists. In one example embodiment, the stored patient identifiers are identified and stored as discussed in steps 314-318 and 324 of FIG. 3 above. In one example embodiment, the comparison can be made by the adherence assessment module 180 or another portion of the service provider computer 106.

In step 430, an inquiry is conducted to determine if the identified one or more patient identifiers from the healthcare claim transaction 206 or adjudicated response 208 matches one or more of the stored patient identifiers from the e-prescription transactions 204 for patients who are to receive adherence assessment evaluations. In one example embodiment, the adherence assessment module 180 or another portion of the service provider computer 106 can determine if a match exists. If the identified one or more patient identifiers does not match a stored patient identifier for a e-prescription transaction, the NO branch can be followed to step 448. If there is a match, the YES branch is followed optionally to step 432 or 438.

In certain example embodiments, the adherence assessment module 180 or another portion of the service provider computer 106 can additionally determine the date of service for the healthcare claim transaction 206 and the date of service for the stored e-prescription transaction 204 record that contains the matching patient identifier. The adherence assessment module 180 or another portion of the service provider computer can then compare the two dates of service to determine if they are within a predetermined threshold amount of time to one another. For example, the predetermined threshold amount can be anywhere between 0-30 days and preferably less than 10 days and more preferably less than 7 days. By comparing the dates of service, the system can increase the likelihood that the received healthcare claim transaction 206 is for the same prescription as that in the stored record for the e-prescription transaction having the matching patient identifier. If the difference in the dates of service between the healthcare claim transaction 206 and the stored record for the e-prescription transaction 204 are less than or equal to the predetermined threshold amount, then the process may continue optionally to step 432 or 438. If the difference is greater than the threshold, then the process may continue to step 448.

In step 432, the identifier for the medication being requested in the healthcare claim transaction 206 or adjudicated response 208 can be identified. For example, the medication identifier can be the NDC code or RxNorm number for the medication and can be included in a predetermined field of the healthcare claim transaction 206 or adjudicated response 208. In addition, or in the alternative, the medication identifier can be the name of the medication. In one example embodiment, the medication identifier can be identified by the adherence assessment module 180 or another portion of the service provider computer 106 based on a review of the data in the predetermined field in the healthcare claim transaction 206 or adjudicated response 208.

In step 434, the adherence assessment module 180 or another portion of the service provider computer 106 can compare the medication identifier in the healthcare claim transaction 206 or the adjudicated response 208 to a table, schedule, or listing of therapeutic categories to determine if the medication is one that is within one of the therapeutic categories and is to receive adherence assessment evaluations. Alternatively, the medication identifier can be compared to a table, schedule, or listing of medication identifiers for medications that are to receive adherence assessment evaluations to determine if a match exists. In another example embodiment, the medication identifier can be compared to the medication identifier in the matching record identified in step 430 to determine the medication identifiers match. For example, the therapeutic categories of interest for adherence assessment can include, but are not limited to, medications for the treatment of hypertension, diabetes, and cholesterol. The therapeutic categories can be presented as categories and the service provider computer 106 or the adherence assessment module 180 can determine the medication identifiers for medications that fall within each therapeutic category and whether the medication identifier in the healthcare claim transaction 206 or adjudicated response 208 matches any of those medication identifiers. Alternatively, the medication identifiers can be provided for each therapeutic category, such as in the patient roster or similar file provided by the payor and the service provider computer 106 or adherence assessment module 180 can determine if the medication identifier in the healthcare claim transaction 206 or adjudicated response 208 matches at least one of the medication identifiers in the therapeutic categories. In another alternative, instead of therapeutic categories, medication identifiers can be provided, irrespective of therapeutic category, such as in the patient roster or similar file, and the service provider computer 106 or adherence assessment module 180 can determine if the medication identifier in the healthcare claim transaction 206 or adjudicated response 208 matches at least one of the medication identifiers. In step 436, an inquiry is conducted to determine if a match to the medication identifier exists. In one example, embodiment, the determination can be made by the adherence assessment module 180 or another portion of the service provider computer 106. If the medication identifier from the healthcare claim transaction 206 or adjudicated response 208 is within one of the predetermined therapeutic categories, matches the medication identifier in the matching record identified in step 430, or otherwise matches medication identifiers for medication to receive adherence assessment evaluations, then the YES branch can be followed to step 438. Otherwise, if the medication identifier does not match or is not included in the therapeutic category, the NO branch is followed to step 448.

In step 438, the adherence assessment module 180 or another portion of the service provider computer 106 can store all or a portion of the transaction data from the healthcare claim transaction 206 and/or the adjudicated response 208. For example, the stored transaction data can include, but is not limited to, the prescription number, the medication identifier, the one or more patient identifiers, the pharmacy identifier, the prescriber identifier, the days' supply, the medication quantity, the number of refills, and the claims processor identifier and can store the transaction data in, for example, the database 182 or the data files 148.

In step 440, an inquiry is conducted to determine if the healthcare claim transaction 206 is for a refill of the medication identified therein. Alternatively, or in addition, a determination can be made if the medication is a maintenance medication. The determination can be made by the adherence assessment module 180 or another portion of the service provider computer 106. For example, the adherence assessment module can parse the healthcare claim transaction 206 to look for refill information in a predetermined filed of the transaction 206, such as the number of refills allowed and the current fill number, to determine if the transaction 206 is for a refill of the medication. If the transaction 206 is for a refill of the medication, the YES branch is followed to step 442. Otherwise, the NO branch is followed to step 444.

In step 442, an evaluation is made to determine the adherence level for the patient with regard to making the current refill. Example embodiments of the evaluation in step 442 are described in greater detail in FIG. 5 below. In certain exemplary embodiments, the evaluation conducted in step 442 is conducted by the adherence assessment module 180 and/or the service provider computer 106. In step 444, the adherence assessment module 180 or another portion of the service provider computer 106 can generate a prescription fill status notification 210. The prescription fill status notification 210 can take the form of a NCPDP Script transaction, an NCPDP Telecommunications transaction, HL7 transaction, an X-12 transaction or some other form of healthcare transaction. Alternatively, the notification 210 can be sent to the prescriber via email, SMS text, MMS text, facsimile transmission, or some other form of digital communications transmission. In one example, the notification 210 can include the patient identifier, medication identifier, prescriber identifier, pharmacy identifier, the date of service for the e-prescription transaction 204 and/or the healthcare claim transaction 206, and, optionally, an adherence level for the patient taking the medication.

In step 446, the adherence assessment module 180 or another portion of the service provider computer 106 can transmit the prescription fill status notification 210 to the prescriber/healthcare provider computer 104B for the prescriber that prescribed the medication in the healthcare claim transaction 206. In one example, the prescriber/healthcare provider computer 104B can receive the notification 210 from the service provider computer 106 via the network 110.

In step 448, the service provider computer 106 can transmit the adjudicated healthcare claim transaction response 208 to the pharmacy/healthcare provider computer 104A via, for example, the network 110. The pharmacy/healthcare provider computer 104A receives the adjudicated healthcare claim transaction response 208 from the service provider computer 106 in step 450. In step 452, the pharmacy, such as a pharmacist or other pharmacy employee can dispense the medication to the patient if the response status in the adjudicated response 208 is an approval or can inform the patient of the rejection if the response status is a rejection. The process then continues to the END step.

Figure 5:
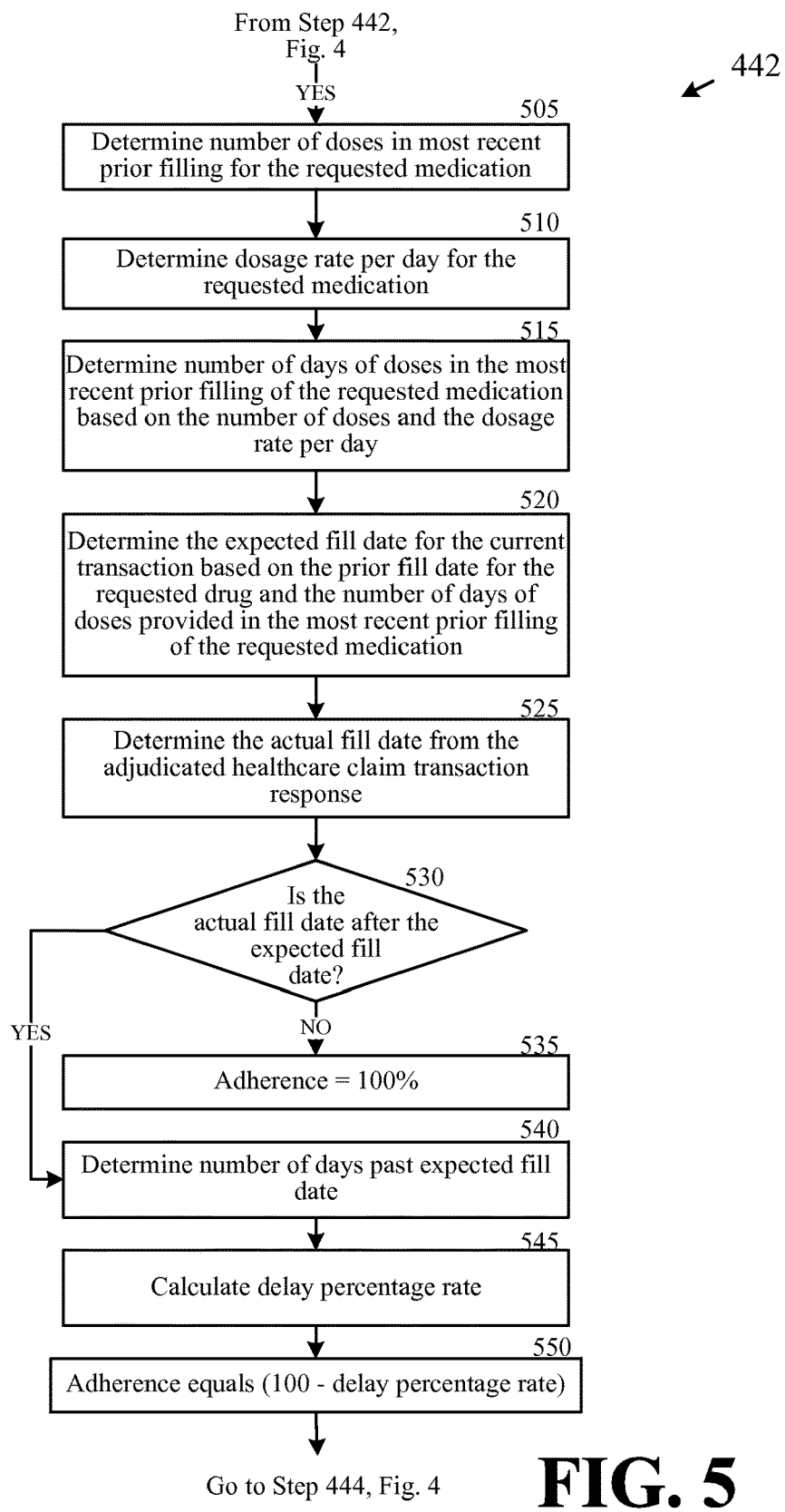
FIG. 5 is a flow chart of an example method for determining the level of adherence for a patient in the timing of the refilling of a prescription medication as part of the processing of the healthcare transaction, according to one exemplary embodiment of the disclosure.

FIG. 5 is a flow chart of the method 442 of FIG. 4 for determining a patient adherence level with regard to requesting a refill of a medication in accordance with one exemplary embodiment of the disclosure. Referring now to FIGS. 1, 2A, 4 and 5, the exemplary method 442 begins at step 505 where a determination is made as to the number of doses that were provided in the most recent prior filling for the patient for the medication requested in the healthcare claim transaction 206. In one exemplary embodiment, the determination is made by the adherence assessment module 180 or another portion of the service provider computer 106 obtaining patient identification information (such as the first and last name of the patient, the date of birth of the patient, the zip code of the patient, and the Cardholder ID for the patient) and medication or service identification information (such as the NDC code for the medication) from the adjudicated healthcare claim transaction response 208 and comparing that information to stored information in the database 182 to determine the timing and dosage amount provided in the last filling for the patient for the same medication as that currently being requested in the healthcare claim transaction 206.

In step 510, the adherence assessment module 180 determines the dosage rate per day for the requested medication based on information contained in the record identified in step 505. A determination of the number of days doses provided to the patient in the most recent prior filling of the requested medication is made based on the number of doses provided and the dosage rate per day identified in steps 505 and 510 respectively in step 515. This determination can be made by the adherence assessment module 180 or another portion of the service provider computer 106. For example, if two hundred doses were provided in the most recent prior filling for the requested drug and the dosage rate is two doses per day, the number of days dosage would be (200 doses/2 doses per day)=100 dosage days. In an alternative embodiment, the dosage days can be directly determined from the record in the database 182 without having to do the calculation. For example, the dosage days provided with each filling for each patient could be stored in the database 182 for subsequent retrieval, as needed, by the adherence assessment module 180. In this alternative embodiment, the steps of determining the number of doses and the dosage rate would not be necessary.

In step 520, the expected fill date for the current transaction is determined by, for example, the adherence evaluation module 180 based on the fill date for the most recent prior filling of the requested medication by the patient and based on the number of dosage days provided in the most recent prior filling of the requested medication. In one exemplary embodiment, the expected fill date is determined by adding the number of dosage days received at the prior fill date to the prior fill date. For example, if the prior fill date was Aug. 20, 2012, and 100 dosage days of the requested medication were provided at the most recent prior fill date, then the expected fill date would be 100 days after Aug. 20, 2012 or Nov. 28, 2012.

The actual fill date for the current transaction is determined in step 525. In one exemplary embodiment, the determination is made by the adherence assessment module 180 or another portion of the service provider computer 106 by parsing the adjudicated healthcare claim transaction response 208 and determining the date of service of the transaction 208 from one of the fields therein. This date will be the actual fill date for the current transaction 206. In step 530, an inquiry is conducted to determine if the actual fill date is after the expected fill date. The inquiry can be conducted by the adherence assessment module 180 or another portion of the service provider computer 106 by comparing the actual fill date and the expected fill date determined in step 520. If the actual fill date is not after the expected fill date, then the NO branch is followed to step 535, where the adherence level for the patient for this transaction is set to one hundred percent. The process then continues to step 444 of FIG. 4.

On the other hand, if the actual fill date is after the expected fill date, then the YES branch is followed to step 540, where the adherence evaluation module 180 or another portion of the service provider computer 106 can determine the number of days that the actual fill date is past the expected fill date. For example, if the actual fill date was Dec. 8, 2012, and the expected fill date was Nov. 28, 2012, then the number of days past the expected fill date (or days late) would be ten. In step 545, the delay percentage rate is calculated. The delay percentage rate can be calculated as the number of days late divided by the number of dosage days of the requested medication provided at the prior fill date. Using the example information above, the delay percentage rate would be calculated as (10/100)=0.10 or 10%. The delay percentage rate is subtracted from one hundred percent in step 550 by, for example, the adherence evaluation module 180 to determine the patient adherence level. Using the example provided above, the patient adherence level for this example would be 100%−10%=90%. The process then continues to step 444 of FIG. 4.

The methods described and shown in FIGS. 3-5 may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3-5 may be performed.

Figure 2B:
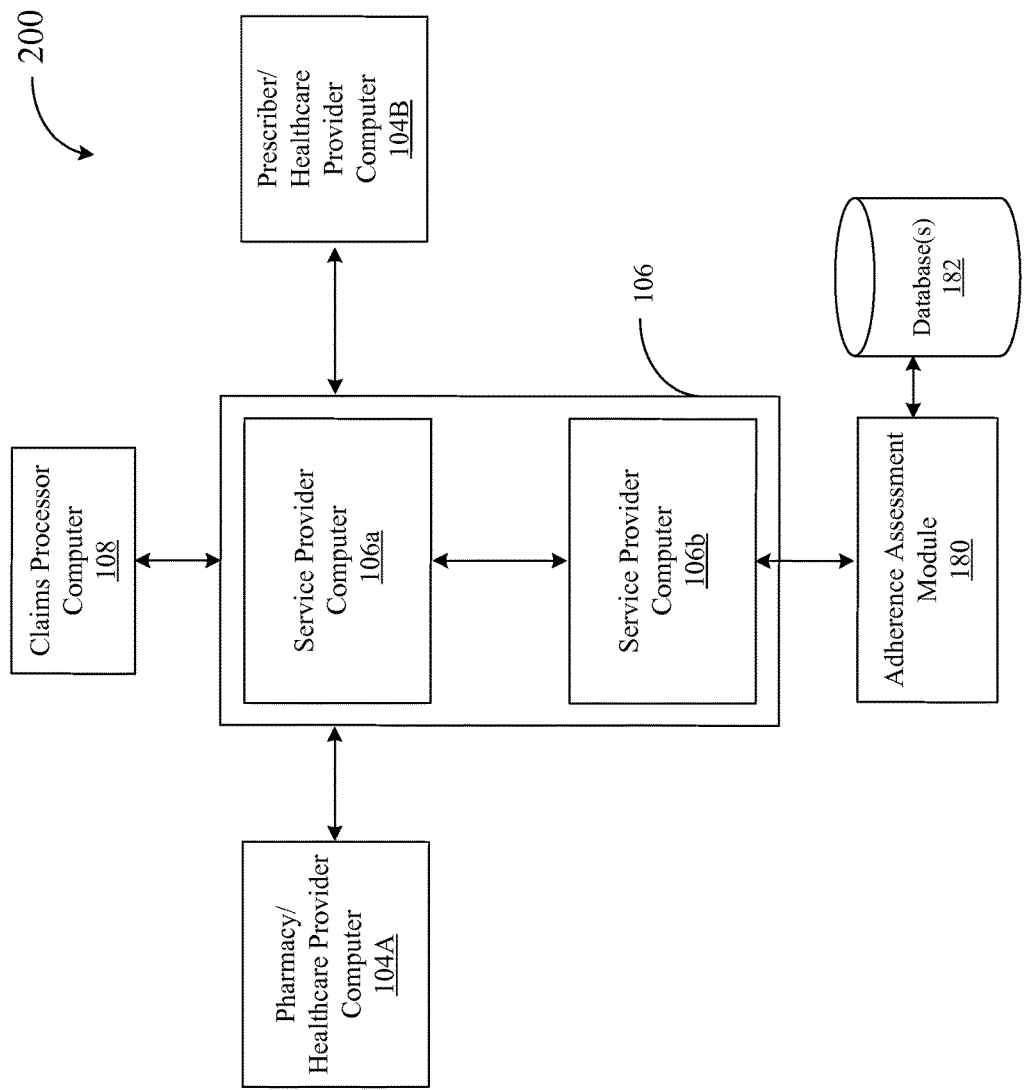
FIG. 2B is a diagram of another example data flow for evaluating healthcare transactions to determine patient adherence to a prescribed medication protocol as part of the processing of the healthcare transaction processed through one or more service providers, according to an alternative exemplary embodiment of the disclosure.

Likewise, while FIGS. 3-5 have been described primarily in conjunction with FIG. 2A, it will be appreciated that variations of FIG. 2A are available. As shown by FIG. 2B, the service provider computer 106 may include two or more distinct service provider computers 106*a* and 106*b* that are in communication with each other. These distinct service provider computers 106*a* and 106*b* may be owned, operated, and or located by the same or distinct and wholly-unrelated companies. The service provider computer 106*a* may be operative with the pharmacy/healthcare provider computer 104A and the prescriber/healthcare provider computer 104B, while the service provider computer 106*b* may be operative with other healthcare provider computers and/or other third-party entity computers. However, the service provider computer 106*b* may have a data processing arrangement with the service provider computer 106*a*. Under the data processing arrangement, the service provider computer 106*a* may be permitted to utilize or offer services of the service provider computer 106*b*, including the operations and use of the adherence assessment module 180 and/or the database 182 to conduct assessments of patient adherence to medication protocols by evaluating healthcare transactions, as discussed above in FIGS. 3-5. Accordingly, the services accessible by the service provider computer 106*b*, including the adherence assessments for patients, may be available to the prescriber/healthcare provider computer 104B via the service provider computers 106*a* and 106*b*.

Accordingly, example embodiments disclosed herein can provide the technical effects of creating a system and methods that provide a real-time or near real time way to evaluate healthcare transactions to determine patient adherence to medication protocols. In this regard, physicians will have a better idea as to whether the medications they are prescribing to their patients are actually being filled by the patient and taken as directed in the prescription. This can help the prescriber determine whether patient issues are due to the medication not working as expected or because the patient is not adhering to the medication protocol for the medication.

While certain example embodiments disclosed herein describe the adherence assessment module 180 as being separate of the service provider computer 106, in alternate embodiments, the adherence assessment module 180 or the functions that it completes may be part of the service provider computer 106. In those embodiments where the adherence assessment module 180 is incorporated into the service provider computer 106, and with regard to the methods described above, the steps describing transmitting or receiving between the service provider computer 106 and the adherence assessment module 180 may be internal transmissions within the service provider computer 106 or may be omitted altogether. Further, while the exemplary embodiments described herein disclose certain steps occurring at the service provider computer 106 and/or the adherence assessment module 180, in alternative embodiments those steps described with reference to FIGS. 1-5 may alternately be completed at a pharmacy/healthcare provider computer 104A, a prescriber/healthcare provider computer 104B, or another healthcare provider computer 104 (e.g., a hospital computer, clinic computer, etc.) a claims processor computer 108, an adherence assessment module 180, any combination thereof, and/or a combination of those devices along with the service provider computer 106. In those alternate embodiments, certain transmission/receiving steps described above with reference to FIGS. 1-5 may be omitted while others may be added, as understood by one or ordinary skill in the art. The intent being that, in alternate embodiments, any of the devices/computers discussed in FIG. 1 are capable of completing all or any part of the methods described with reference to FIGS. 2A-5.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, that includes a computer usable medium (e.g., transitory or non-transitory) having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method, comprising:
receiving one or more patient rosters that identifies patients for which a payor wants an adherence assessment to be completed;
receiving, by one or more service provider computers comprising a switch or a router and associated with a service provider and comprising one or more processors from a prescriber computer for a prescriber of medication to a patient, an e-prescription transaction comprising prescription data, wherein the prescription data comprises a first medication identifier identifying a medication to be prescribed and a first patient identifier identifying the patient to receive the medication prescribed to the patient by the prescriber;
in an instance in which (i) the first patient identifier matches a patient from the one or more patient rosters or (ii) the first medication identifier is within a predetermined therapeutic category or matches a medication identifier for medication to receive adherence assessment evaluations, selectively storing information from the e-prescription transaction;
transmitting, by the one or more service provider computers, the e-prescription transaction to a pharmacy computer for a pharmacy, wherein the one or more service provider computers comprises one or more memory devices configured to store data files that include a routing table to identify a destination of communications and a network interface to facilitate connection of the one or more service provider computers with one or more networks;
receiving, by the one or more service provider computers from the pharmacy computer, a healthcare claim transaction comprising claim transaction data, wherein the claim transaction data comprises a second medication identifier and a second patient identifier;
transmitting, by the one or more service provider computers, the healthcare claim transaction to a claims processor computer of a claims processor for adjudication;
receiving, by the one or more service provider computers from the claims processor computer, an adjudicated healthcare claim transaction response for the healthcare claim transaction; and
determining whether a reversal transaction for the healthcare claim transaction has been received within a predetermined amount of time from receipt of the adjudicated healthcare claim transaction response and only in an instance in which the reversal transaction has not been received within the predetermined amount of time:
comparing, by the one or more service provider computers, the first patient identifier to the second patient identifier to determine if the first patient identifier matches the second patient identifier;
determining, by the one or more service provider computers and based on the comparison of the first patient identifier to the second patient identifier, if the first patient identifier from the e-prescription transaction matches the second patient identifier from the healthcare claim transaction;
comparing, by the one or more service provider computers, a first date of service for the e-prescription transaction and a second date of service for the healthcare claim transaction;
determining, by the one or more service provider computers and based on the comparison of the first date of service to the second date of service, if the first date of service is within a predetermined threshold amount of time of the second date of service;
in an instance in which the first patient identifier from the e-prescription transaction matches the second patient identifier from the healthcare claim transaction and the first date of service for the e-prescription transaction is within the predetermined threshold amount of time of the second date of service for the healthcare claim transaction, selectively storing at least a portion of the claim transaction data from the healthcare claim transaction;
generating, by the one or more service provider computers and based at least in part on the positive determination that the first patient identifier from the e-prescription transaction matches the second patient identifier from the healthcare claim transaction and the determination that the first date of service for the e-prescription transaction is within the predetermined threshold amount of time of the second date of service for the healthcare claim transaction, a prescription fill notification;

transmitting, by the one or more service provider computers, the prescription fill notification to the prescriber computer;

with reference to a table, list or schedule, stored in a database, of therapeutic categories for which adherence assessments are to be completed for a respective patient, determining if the first medication identifier identifies a medication that is in a therapeutic category for which adherence assessments are to be completed; and providing the adherence assessment based at least in part on a positive determination that the first medication identifier identifies a medication in a therapeutic category for which adherence assessments are to be completed.

2. The computer-implemented method of claim 1, further comprising:

identifying, by the one or more service provider computers, the first medication identifier in the e-prescription transaction.

3. The computer-implemented method of claim 1, further comprising:

determining, by the one or more service provider computers and based on the e prescription data, a receiving pharmacy for the e-prescription transaction, wherein the receiving pharmacy is the pharmacy.

4. The computer-implemented method of claim 1, wherein the prescription fill notification comprises the first patient identifier, the first medication identifier, the first date of service for the e-prescription transaction, and the second date of service for the healthcare claim transaction.

5. The computer-implemented method of claim 1, further comprising:

determining, by the one or more service provider computers based on the claim transaction data, if the healthcare claim transaction is for a refill of the medication;

calculating, by the one or more service provider computers, a medication adherence level for the patient based at least in part of a positive determination that the healthcare claim transaction is for the refill of the medication; and wherein the prescription fill notification comprises the medication adherence level.

6. The computer-implemented method of claim 5, wherein calculating the medication adherence level for the patient comprises:

determining, by the one or more service provider computers, an actual fill date and an expected fill date for the medication;

determining, by the one or more service provider computers, if the actual fill date is after the expected fill date;

determining, by the one or more service provider computers, a number of days the actual fill date is after the expected fill date based on positive determination that the actual fill date is after the expected fill date;

calculating, by the one or more service provider computers, a delay percentage rate based on the number of days the actual fill date is after the expected fill date and a number of dosage days of the medication provided at the most recent prior fill date; and calculating, by the one or more service provider computers, the medication adherence level for the patient as the difference between one hundred percent and the delay percentage rate.

7. The computer-method of claim 6, wherein determining the expected fill date for the medication comprises:

determining, by the one or more service provider computers and based at least in part on the claim transaction data, a most recent prior fill date for the medication;

determining, by the one or more service provider computers, a number of dosage days medication provided at the most recent prior fill date; and determining, by the one or more service provider computers, an expected fill date for the medication based on the most recent prior fill date and the number of dosage days for the medication provided at the most recent prior fill date.

8. A system comprising a switch or a router, the system comprising:

at least one memory operable to store computer-executable instructions and configured to store data files that include a routing table to identify a destination of communications;

a database storing a table, list or schedule of therapeutic categories for which adherence assessments are to be completed for a respective patient;

a network interface to facilitate connection with one or more networks; and at least one processor configured to access the at least one memory and execute the computer-executable instructions to:

receive one or more patient rosters that identifies patients for which a payor wants an adherence assessment to be completed;

receive, from a prescriber computer for a prescriber of medication to a patient, an e-prescription transaction comprising prescription data, wherein the prescription data comprises a first medication identifier identifying a medication to be prescribed and a first patient identifier identifying the patient to receive the medication prescribed to the patient by the prescriber;

in an instance in which (i) the first patient identifier matches a patient from the one or more patient rosters or (ii) the first medication identifier is within a predetermined therapeutic category or matches a medication identifier for medication to receive adherence assessment evaluations, selectively store information from the e-prescription transaction;

direct communication of the e-prescription transaction to a pharmacy computer for a pharmacy;

receive, from the pharmacy computer, a healthcare claim transaction comprising claim transaction data, wherein the claim transaction data comprises a second medication identifier and a second patient identifier;

direct communication of the healthcare claim transaction to a claims processor computer of a claims processor for adjudication;

receive, from the claims processor computer, an adjudicated healthcare claim transaction response for the healthcare claim transaction; and determine whether a reversal transaction for the healthcare claim transaction has been received within a predetermined amount of time from receipt of the adjudicated healthcare claim transaction response and only in an instance in which the reversal transaction has not been received within the predetermined amount of time:
  compare the first patient identifier to the second patient identifier to determine if the first patient identifier matches the second patient identifier;
  determine, based on the comparison of the first patient identifier to the second patient identifier, if the first patient identifier from the e-prescription transaction matches the second patient identifier from the healthcare claim transaction;
  compare, by the one or more service provider computers, a first date of service for the e-prescription transaction and a second date of service for the healthcare claim transaction;
  determine, by the one or more service provider computers and based on the comparison of the first date of service to the second date of service, if the first date of service is within a predetermined threshold amount of time of the second date of service;
  in an instance in which the first patient identifier from the e-prescription transaction matches the second patient identifier from the healthcare claim transaction and the first date of service for the e-prescription transaction is within the predetermined threshold amount of time of the second date of service for the healthcare claim transaction, selectively store at least a portion of the claim transaction data from the healthcare claim transaction;
  generate, based at least in part on the positive determination that the first patient identifier from the e-prescription transaction matches the second patient identifier from the healthcare claim transaction and the determination that the first date of service for the e-prescription transaction is within the predetermined threshold amount of time of the second date of service for the healthcare claim transaction, a prescription fill notification;
  direct communication of the prescription fill notification to the prescriber computer;
  determine if the first medication identifier identifies a medication that is in a therapeutic category for which adherence assessments are to be completed; and
  provide the adherence assessment based at least in part on a positive determination that the first medication identifier identifies a medication in a therapeutic category for which adherence assessments are to be completed.

9. The system of claim 8, wherein the at least one processor is further configured to access the at least one memory and execute the computer-executable instructions to:
  identify the first medication identifier in the e-prescription transaction.

10. The system of claim 8, wherein the at least one processor is configured to access the at least one memory and execute the computer-executable instructions to:
  determine, based on the e-prescription data, a receiving pharmacy for the e-prescription transaction, wherein the receiving pharmacy is the pharmacy.

11. The system of claim 8, wherein the prescription fill notification comprises the first patient identifier, the first medication identifier, the first date of service for the e-prescription transaction, and the second date of service for the healthcare claim transaction.

12. The system of claim 8, wherein the at least one processor is configured to access the at least one memory and execute the computer-executable instructions to:
  determine, based on the claim transaction data, if the healthcare claim transaction is for a refill of the medication;
  calculate a medication adherence level for the patient based at least in part of a positive determination that the healthcare claim transaction is for the refill of the medication,
  wherein the prescription fill notification comprises the medication adherence level.

13. The system of claim 12, wherein the at least one processor is configured to calculate the medication adherence level for the patient by accessing the at least one memory and executing the computer-executable instructions to:
  determine an actual fill date and an expected fill date for the medication;
  determine if the actual fill date is after the expected fill date;
  determine a number of days the actual fill date is after the expected fill date based on positive determination that the actual fill date is after the expected fill date;
  calculate a delay percentage rate based on the number of days the actual fill date is after the expected fill date and a number of dosage days of the medication provided at the most recent prior fill date; and
  calculate the medication adherence level for the patient as the difference between one hundred percent and the delay percentage rate.

14. The system of claim 13, wherein the at least one processor is configured to determine the expected fill date for the medication by accessing the at least one memory and executing the computer-executable instructions to:
  determine, based at least in part on the claim transaction data, a most recent prior fill date for the medication;
  determine a number of dosage days medication provided at the most recent prior fill date; and
  determine an expected fill date for the medication based on the most recent prior fill date and the number of dosage days for the medication provided at the most recent prior fill date.

* * * * *